(12) United States Patent
Voss et al.

(10) Patent No.: US 11,702,631 B2
(45) Date of Patent: Jul. 18, 2023

(54) ANTIGEN RECEPTORS AND USES THEREOF

(71) Applicants: BIONTECH CELL & GENE THERAPIES GMBH, Mainz (DE); TRON—TRANSLATIONALE ONKOLOGIE AN DER UNIVERSITÄTSMEDIZIN DER JOHANNES GUTENBERG-UNIVERSITAT MAINZ GEMEINNUTZIGE GMBH, Mainz (DE)

(72) Inventors: Ralf Holger Voss, Ingelheim (DE); Ugur Sahin, Mainz (DE); Petra Oehm, Mainz (DE); Matthias Birtel, Mainz (DE); Janina Caspar, Waldalgesheim (DE)

(73) Assignees: TRON—TRANSLATIONALE ONKOLOGIE AN DER UNIVERSITATSMEDIZIN DER JOHANNES GUTENBERG-UNIVERSITAT MAINZ GEMEINNUTZIGE GMBH; BIONTECH CELL & GENE THERAPIES GMBH

( * ) Notice: Subject to any disclaimer, the term of this patent is extended or adjusted under 35 U.S.C. 154(b) by 738 days.

(21) Appl. No.: 16/493,618

(22) PCT Filed: Mar. 14, 2018

(86) PCT No.: PCT/EP2018/056399
§ 371 (c)(1),
(2) Date: Sep. 12, 2019

(87) PCT Pub. No.: WO2018/167151
PCT Pub. Date: Sep. 20, 2018

(65) Prior Publication Data
US 2020/0063101 A1 Feb. 27, 2020

(30) Foreign Application Priority Data
Mar. 15, 2017 (WO) .................. PCT/EP2017/056086

(51) Int. Cl.
| | |
|---|---|
| C07K 14/705 | (2006.01) |
| C07K 19/00 | (2006.01) |
| C12N 5/0783 | (2010.01) |
| C07K 14/725 | (2006.01) |
| C07K 16/28 | (2006.01) |
| C12N 15/90 | (2006.01) |
| A61K 38/00 | (2006.01) |

(52) U.S. Cl.
CPC ........ *C12N 5/0636* (2013.01); *C07K 14/7051* (2013.01); *C07K 14/70521* (2013.01);
(Continued)

(58) Field of Classification Search
CPC ... A61K 38/00; A61P 35/00; C07K 14/70503; C07K 14/7051; C07K 14/70521;
(Continued)

(56) References Cited

U.S. PATENT DOCUMENTS

| 3,409,577 A1 | 4/2013 | Armstrong |
| 2003/0118592 A1 | 6/2003 | Ledbetter et al. |

(Continued)

FOREIGN PATENT DOCUMENTS

| EP | 2 502 934 | 9/2012 |
| WO | 2000/023087 | 4/2000 |

(Continued)

OTHER PUBLICATIONS

The International Search Report (ISR) with Written Opinion for PCT/EP2018/056399 dated Apr. 16, 2018, pp. 1-11.
(Continued)

*Primary Examiner* — Jeffrey E. Russel
(74) *Attorney, Agent, or Firm* — McDonnell Boehnen Hulbert & Berghoff LLP

(57) ABSTRACT

The present invention generally embraces the treatment of diseases by targeting cells expressing an antigen on the cell
(Continued)

surface. In particular the invention relates to recombinant antigen receptors and uses thereof. T cells engineered to express such antigen receptors are useful in the treatment of diseases characterized by expression of one or more antigens bound by the antigen receptors.

15 Claims, 16 Drawing Sheets

Specification includes a Sequence Listing.

(52) U.S. Cl.
CPC .............. *C07K 16/28* (2013.01); *C12N 15/90* (2013.01); *A61K 38/00* (2013.01); *C07K 2319/02* (2013.01); *C07K 2319/03* (2013.01); *C07K 2319/70* (2013.01)

(58) Field of Classification Search
CPC ................ C07K 16/28; C07K 2319/00; C07K 2319/02; C07K 2319/03; C07K 2319/70; C12N 5/0636; C12N 15/90
See application file for complete search history.

(56) References Cited

U.S. PATENT DOCUMENTS

| | | | |
|---|---|---|---|
| 2003/0133939 A1 | 7/2003 | Ledbetter et al. | |
| 2009/0324538 A1 | 12/2009 | Wong et al. | |
| 2010/0278774 A1* | 11/2010 | Wong | C07K 14/5443 435/348 |

FOREIGN PATENT DOCUMENTS

| | | | |
|---|---|---|---|
| WO | 2016/187349 | 11/2016 | |
| WO | 2016180778 | 11/2016 | |
| WO | WO-2016187349 A1 * | 11/2016 | ......... A61K 39/0011 |
| WO | 2017/059900 | 4/2017 | |

OTHER PUBLICATIONS

Barrett, David M. et al. "Chimeric antigen receptor (CAR) and T cell receptor (TCR) Modified T cells Enter Main Street and Wall Street" The Journal of Immunology (2015) vol. 195(3), pp. 755-761.

Cohen, Cyrille J. et al. "Enhanced Antitumor Activity of T Cells Engineered to Express T-Cell Receptors with a Second Disulfide Bond" Cancer Research (2007) vol. 67(8), pp. 3898-3903.

Gross, Gideon et al. "Endowing T cells with antibody specificity using chimeric T cells receptors" The FASEB Journal (1992) vol. 6(15), pp. 3370-1178.

Kershaw, Michael H. et al. "Gene-engineered T cells for cancer Therapy" Nature Reviews Cancer (2013) vol. 13(8), pp. 525-541.

Harris, et al., "Adoptive T Cell Therapies: A Comparison of T Cell Receptors and Chimeric Antigen Receptors," Trends Pharmacol Sci. Mar. 2016 ; 37(3): 220-230.

Rosano et al., "Recombinant protein expression in *Escherichia coli*: advances and challenges," Frontiers in Microbiology. Apr. 2014; vol. 5, article 172, pp. 1-17.

Zhao, et al. (Nov. 2009) "A Herceptin-Based Chimeric Antigen Receptor with Modified Signaling Domains Leads to Enhanced Survival of Transduced T Lymphocytes and Antitumor Activity," J Immunol 183(9): 5563-5574.

* cited by examiner

D     Classical scCAR Cl6

Prior art

E     Inter-combinatory Cα/β - CAR Cl6

Prior art

H        Inter-combinatory TCR - CAR Cl6

I        Inter-combinatory TCR - CAR Cl6 silCDR3α

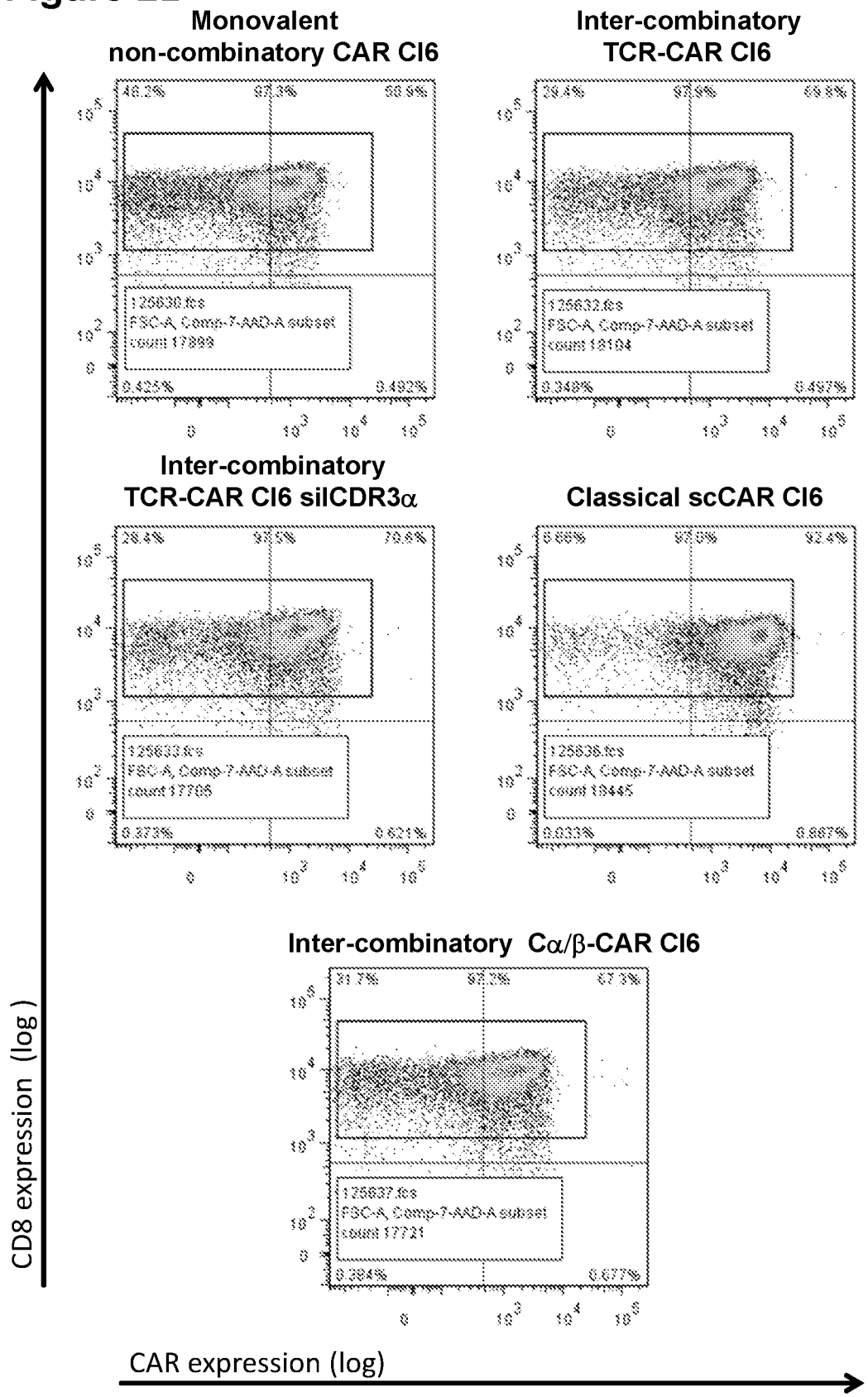

ANTIGEN RECEPTORS AND USES THEREOF

CROSS-REFERENCE TO RELATED APPLICATION

This application is a U.S. national phase of International Application No. PCT/EP2018/056399, filed Mar. 14, 2018, which is incorporated by reference herein in its entirety.

SEQUENCE LISTING STATEMENT

A computer readable form of the Sequence Listing is filed with this application by electronic submission and is incorporated into this application by reference in its entirety. The Sequence Listing is contained in the file created on Aug. 15, 2022 having the file name "19-1579-PCT-US_SeqList_ST25.txt" and is 1 kb in size.

TECHNICAL FIELD OF THE INVENTION

The present invention relates to recombinant antigen receptors and uses thereof. T cells engineered to express such antigen receptors are useful in the treatment of diseases characterized by expression of one or more antigens bound by the antigen receptors.

BACKGROUND OF THE INVENTION

T cells play a central role in cell-mediated immunity in humans and animals. The recognition and binding of a particular antigen is mediated by the T cell receptors (TCRs) expressed on the surface of T cells. The TCR of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell.

The TCR is a part of a complex signaling machinery, which includes the heterodimeric complex of the TCR α- and β-chains, the co-receptor CD4 or CD8 and the CD3 signal transduction module. The TCR α/β heterodimer is responsible for antigen recognition and relaying the activation signal through the cell membrane in concert with CD3, while the CD3 chains themselves transfer the incoming signal to adaptor proteins inside the cell. Thus, the transfer of the TCR α/β chains offers the opportunity to redirect T cells towards any antigen of interest.

Adoptive cell transfer (ACT) based immunotherapy can be broadly defined as a form of passive immunization with previously sensitized T cells that are transferred to non-immune recipients or to the autologous host after ex vivo expansion from low precursor frequencies to clinically relevant cell numbers. Cell types that have been used for ACT experiments include lymphokine-activated killer (LAK) cells (Mule, J. J. et al. (1984) Science 225, 1487-1489; Rosenberg, S. A. et al. (1985) N. Engl. J. Med. 313, 1485-1492), tumor-infiltrating lymphocytes (TILs) (Rosenberg, S. A. et al. (1994) J. Natl. Cancer Inst. 86, 1159-1166), donor lymphocytes after hematopoietic stem cell transplantation (HSCT) as well as tumor-specific T cell lines or clones (Dudley, M. E. et al. (2001) J. Immunother. 24, 363-373; Yee, C. et al. (2002) Proc. Natl. Acad. Sci. U.S.A 99, 16168-16173). Adoptive T cell transfer was shown to have therapeutic activity against human viral infections such as CMV. For adoptive immunotherapy of melanoma Rosenberg and co-workers established an ACT approach relying on the infusion of in vitro expanded autologous tumor-infiltrating lymphocytes (TILs) isolated from excised tumors in combination with a non-myeloablative lymphodepleting chemotherapy and high-dose IL2. A clinical study resulted in an objective response rate of ~50% of treated patients suffering from metastatic melanoma (Dudley, M. E. et al. (2005) J. Clin. Oncol. 23: 2346-2357).

An alternative approach is the adoptive transfer of autologous T cells reprogrammed to express a tumor-reactive immunoreceptor of defined specificity during short-time ex vivo culture followed by reinfusion into the patient (Kershaw M. H. et al. (2013) Nature Reviews Cancer 13 (8): 525-41). This strategy makes ACT applicable to a variety of common malignancies even if tumor-reactive T cells are absent in the patient. Since the antigenic specificity of T cells is rested entirely on the heterodimeric complex of the TCR α- and β-chain, the transfer of cloned TCR genes into T cells offers the potential to redirect them towards any antigen of interest. Therefore, TCR gene therapy provides an attractive strategy to develop antigen-specific immunotherapy with autologous lymphocytes as treatment option. Major advantages of TCR gene transfer are the creation of therapeutic quantities of antigen-specific T cells within a few days and the possibility to introduce specificities that are not present in the endogenous TCR repertoire of the patient. Several groups demonstrated, that TCR gene transfer is an attractive strategy to redirect antigen-specificity of primary T cells (Morgan, R. A. et al. (2003) J. Immunol. 171, 3287-3295; Cooper, L. J. et al. (2000) J. Virol. 74, 8207-8212; Fujio, K. et al. (2000) J. Immunol. 165, 528-532; Kessels, H. W. et al. (2001) Nat. Immunol. 2, 957-961; Dembic, Z. et al. (1986) Nature 320, 232-238). Feasibility of TCR gene therapy in humans was initially demonstrated in clinical trials for the treatment of malignant melanoma by Rosenberg and his group. The adoptive transfer of autologous lymphocytes retrovirally transduced with melanoma/melanocyte antigen-specific TCRs resulted in cancer regression in up to 30% of treated melanoma patients (Morgan, R. A. et al. (2006) Science 314, 126-129; Johnson, L. A. et al. (2009) Blood 114, 535-546). In the meantime clinical testing of TCR gene therapy was extended also to cancers other than melanoma targeting many different tumor antigens (Park, T. S. et al., (2011) Trends Biotechnol. 29, 550-557).

The use of genetic engineering approaches to insert antigen-targeted receptors of defined specificity into T cells has greatly extended the potential capabilities of ACT. Chimeric antigen receptors (CARs) are a type of antigen-targeted receptor composed of intracellular T cell signaling domains fused to extracellular antigen-binding domains, most commonly single-chain variable fragments (scFv's) from monoclonal antibodies. CARs directly recognize cell surface antigens, independent of MHC-mediated presentation, permitting the use of a single receptor construct specific for any given antigen in all patients. Initial CARs fused antigen-recognition domains to the CD3 activation chain of the T cell receptor (TCR) complex. Subsequent CAR iterations have included secondary costimulatory signals in tandem with CD3, including intracellular domains from CD28 or a variety of TNF receptor family molecules such as 4-1BB (CD137) and OX40 (CD134). Further, third generation receptors include two costimulatory signals in addition to CD3, most commonly from CD28 and 4-1BB. Second and third generation CARs dramatically improved antitumor efficacy in vitro and in vivo (Zhao et al., (2009) J. Immunol., (183) 5563-5574), in some cases inducing complete remissions in patients with advanced cancer (Porter et al., (2011) N. Engl. J. Med., (365) 725-733).

A classical CAR consists of an antigen-specific single chain antibody (scFv) fragment, fused to a transmembrane and signaling domain such as CD3. Upon introduction into T cells it is expressed as a membrane-bound protein and induces immune responses upon binding to its cognate antigen (Eshhar et al., (1993) PNAS, (90) 720-724). The induced antigen-specific immune response results in the activation of cytotoxic CD8+ T cells which in turn leads to the eradication of cells expressing the specific antigen, such as tumor cells or virus-infected cells expressing the specific antigen. However, these classical CAR constructs do not activate/stimulate the T cells through their endogenous CD3 complex, which is normally essential for T cell activation. Due to the fusion of the antigen binding domain to CD3, T cell activation is induced through a biochemical "short circuit" (Aggen et al., (2012) Gene Therapy, (19) 365-374). This non-physiological activation of T cells poses a risk for the patient being treated this way since over-activation of T cells may lead to unwanted side effects. For example, long-term basal activation of recombinant T cells due to CAR expression has been observed in vitro ("tonic signaling"), which resulted in an increased accumulation of inhibitory molecules, such as LAG-3, TIM-3 and PD-1, on the surface of recombinant CAR-expressing T cells, which in turn resulted in prematurely exhausted T-cells subsequently leading to a strong negative impact on the response against tumor cells in vivo (Long et al., (2015) Nat. Med., (21) 581-590). This adverse reaction has been associated with an irregular clustering of scFv-fragments through framework residues of this antibody. Additionally, while classic CAR constructs of this type have been successfully tested against different neoplasias, such as leukemia (Porter et al., (2011) N. Engl. J. Med., (365) 725-733), they have also resulted in fatal autoimmune diseases due to basal expression of the targeted antigen (targeted tumor antigen) in normal tissues (on-target/off-tumor-reaction; Morgan et al., (2010) Mol Ther., (18) 843-51).

An alternative approach, in which activation of the T cell occurs through a more physiological mechanism, was the provision of an analogous single chain-TCR (scTv)-fragment fused to the CP constant domain derived from the T cell receptor (TCR) and its co-expression with a TCR-derived Cα constant domain (Voss et al., (2010) Blood, (115) 5154-5163), the latter which recruits the essential endogenous CD3 homodimer (Call et al., (2002) Cell, (111) 967-79). However, in order for these constructs to function as immune system activators, it was essential that their constant domains originate from murine TCRs or need to be murinized (Cohen et al., (2006) Cancer Res., (66) 8878-86; Bialer et al., (2010) J. Immunol., (184) 6232-41) to achieve chain pairing between the scTCR and Cα. The fact that these constructs must have xenogenic sequences for functionality raises the risk that the immune system will react against them when administered and impairs or destroys their therapeutic effectiveness.

Thus, there is a need for the provision of alternate recombinant antigen receptors, in which, e.g., the receptor, upon antigen binding, is sufficiently able to activate the T cell in which it is expressed in a normal physiological manner through the endogenous CD3 complex and, optionally, with no requirement for the presence of any amino acid sequences not of human origin, at least in the signal transmission domain of the antigen receptor, that could induce an unwanted immune response against the recombinant antigen receptor itself.

DESCRIPTION OF INVENTION

Summary of the Invention

The present invention relates to recombinant antigen receptors having at least two antigen binding sites. The antigen receptors comprise two peptide chains. The peptide chains each comprise at least two domains, in addition to a variable region of a T cell receptor chain or a portion thereof, and an immunoreceptor signal transmission domain, in which each of the two domains on one peptide chain forms an antigen binding site with one of the domains on the other peptide chain. In one embodiment, the antigen receptor of the invention has the structure of a T cell receptor wherein the chains thereof each comprise said at least two domains forming the antigen binding sites, preferably at the N terminus of the T cell receptor chains.

In one aspect, the present invention relates to an antigen receptor, which receptor comprises a first peptide chain and a second peptide chain, wherein the first peptide chain comprises a first domain, a second domain, a variable region of a T cell receptor chain or a portion thereof, and an immunoreceptor signal transmission domain; the second peptide chain comprises a first domain, a second domain, a variable region of a T cell receptor chain or a portion thereof, and an immunoreceptor signal transmission domain; wherein the first domain from the first peptide chain forms together with one of the domains from the second peptide chain a first antigen binding site, and wherein the second domain from the first peptide chain forms together with the other domain from the second peptide chain a second antigen binding site. In the antigen receptor of this aspect, the domains forming the respective antigen binding sites are preferably located on different peptide chains. Consequently, antigen binding sites are formed by intermolecular interaction of domains.

In one embodiment, the first and/or second domains each comprise a variable region of an immunoglobulin chain or a variable region of a T cell receptor chain or a portion of the variable region.

In one embodiment, one of the domains forming the first antigen binding site comprises a variable region of a heavy chain of an immunoglobulin with a specificity for an antigen or a portion thereof and the other domain forming the first antigen binding site comprises a variable region of a light chain of an immunoglobulin with a specificity for the antigen or a portion thereof. In one embodiment, one of the domains forming the second antigen binding site comprises a variable region of a heavy chain of an immunoglobulin with a specificity for an antigen or a portion thereof and the other domain forming the second antigen binding site comprises a variable region of a light chain of an immunoglobulin with a specificity for the antigen or a portion thereof.

In one embodiment, the first domain from the first peptide chain comprises a variable region of a heavy chain of an immunoglobulin with a specificity for an antigen or a portion thereof and the domain from the second peptide chain forming an antigen binding site with the first domain from the first peptide chain comprises a variable region of a light chain of an immunoglobulin with a specificity for the antigen or a portion thereof. In one embodiment, the second domain from the first peptide chain comprises a variable region of a heavy chain of an immunoglobulin with a specificity for an antigen or a portion thereof and the domain from the second peptide chain forming an antigen binding site with the second domain from the first peptide chain comprises a variable region of a light chain of an immunoglobulin with a specificity for the antigen or a portion thereof.

In one embodiment, the first and the second domains from the first peptide chain each comprise a variable region of a heavy chain of an immunoglobulin or a portion thereof and the first and the second domains from the second peptide chain each comprise a variable region of a light chain of an immunoglobulin or a portion thereof.

In one embodiment, the N-terminal domain from the first peptide chain forms together with the N-terminal domain from the second peptide chain an antigen binding site; and the C-terminal domain from the first peptide chain forms together with the C-terminal domain from the second peptide chain an antigen binding site.

In one embodiment, the N-terminal domain from the first peptide chain forms together with the C-terminal domain from the second peptide chain an antigen binding site; and the C-terminal domain from the first peptide chain forms together with the N-terminal domain from the second peptide chain an antigen binding site.

In one embodiment of the antigen receptors of the invention, the immunoreceptor signal transmission domain comprises a constant or invariant region of a T cell receptor chain or a constant or invariant region of an immune cell Fc receptor chain or a portion of the constant or invariant region. In one embodiment of the antigen receptors of the invention, (i) the first peptide chain comprises a variable region of a T cell receptor alpha chain or a portion thereof and a constant region of a T cell receptor alpha chain or a portion thereof and the second peptide chain comprises a variable region of a T cell receptor beta chain or a portion thereof and a constant region of a T cell receptor beta chain or a portion thereof, or (ii) the first peptide chain comprises a variable region of a T cell receptor beta chain or a portion thereof and a constant region of a T cell receptor beta chain or a portion thereof and the second peptide chain comprises a variable region of a T cell receptor alpha chain or a portion thereof and a constant region of a T cell receptor alpha chain or a portion thereof. In this embodiment, the variable region of a T cell receptor alpha chain or a portion thereof and the constant region of a T cell receptor alpha chain or a portion thereof corresponds or essentially corresponds to the alpha chain of a T cell receptor, and the variable region of a T cell receptor beta chain or a portion thereof and the constant region of a T cell receptor beta chain or a portion thereof corresponds or essentially corresponds to the beta chain of a T cell receptor, preferably the same T cell receptor from which the alpha chain of a T cell receptor is derived. The domains forming the antigen binding sites are preferably fused at the N terminus of the chains, optionally separated by a linker.

In one embodiment of the antigen receptors of the invention, the variable region of a T cell receptor chain or a portion thereof, and/or the immunoreceptor signal transmission domain such as the constant region of a T cell receptor or a portion thereof is of human origin. Thus, the chain of a T cell receptor to which the variable region of a T cell receptor chain or a portion thereof and the constant region of a T cell receptor chain or a portion thereof may correspond or essentially correspond may be of human origin.

In one embodiment, an antigen receptor of the invention comprises (a) linker(s) connecting domains of the antigen receptor. In one embodiment, an antigen receptor of the invention comprises one or more linkers between the domains forming the antigen binding sites and/or between the domains forming the antigen binding sites and the variable regions of a T cell receptor chain or a portion thereof. The linker can be an arbitrary amino acid sequence of any length so long as it does not interfere with the functions of the antigen receptor, such as the ability of the antigen receptor to bind antigen or to associate with the endogenous CD3 complex, or interfere with the ability of the antigen receptor to induce an immune response upon antigen binding.

In one embodiment of the antigen receptors of the invention, the first and second antigen binding sites bind to the same antigen or different antigens. In one embodiment of the antigen receptors of the invention, the first and second antigen binding sites bind to different epitopes on the same antigen. Consequently, while the domains forming the first antigen binding site are preferably derived from the same immunoglobulin and the domains forming the second antigen binding site are preferably derived from the same immunoglobulin, the domains forming the first antigen binding site and the domains forming the second antigen binding site are derived from the same or different immunoglobulins, said different immunoglobulins binding to the same or different antigens.

In one embodiment, the antigen is a disease-specific antigen, preferably a tumor antigen. In one embodiment, the antigen is expressed on the surface of a cell.

In one aspect, the present invention relates to a peptide chain of the antigen receptors of the invention. In one embodiment, the present invention relates to a peptide chain comprising a first and a second domain which each comprise a variable region of a heavy chain of an immunoglobulin or a portion thereof or each comprise a variable region of a light chain of an immunoglobulin or a portion thereof and wherein the peptide chain further comprises a variable region of a T cell receptor chain or a portion thereof, and an immunoreceptor signal transmission domain such as a constant region of a T cell receptor chain or a portion thereof. Further embodiments of the peptide chains of the invention are as described herein for the antigen receptors of the invention.

In one aspect, the present invention relates to a cell, in particular an immune effector cell such as a T cell, genetically modified to express an antigen receptor of the invention. In one aspect, the present invention relates to a recombinant cell, in particular an immune effector cell such as a T cell, expressing the first peptide chain, the second peptide chain or both the first and second peptide chains of an antigen receptor of the invention or expressing a peptide chain of the invention. Further embodiments of the cell or recombinant cell of the invention are as described herein for the antigen receptors of the invention or the peptide chains of the invention.

In one aspect, the present invention relates to a method for producing a cell expressing an antigen receptor of the invention, the method comprising: (a) providing a cell; (b) providing a first genetic construct encoding the first peptide chain of an antigen receptor of the invention; (c) providing a second genetic construct encoding the second peptide chain of an antigen receptor of the invention; (d) introducing the first and second genetic constructs into the cell; and (e) allowing the constructs to be expressed in the cell. In one embodiment, the present invention relates to a method for producing a cell expressing an antigen receptor which receptor comprises a first peptide chain and a second peptide chain, the method comprising: (a) providing a cell; (b) providing a first genetic construct encoding the first peptide chain comprising a first domain, a second domain, a variable region of a T cell receptor chain or a portion thereof, and an immunoreceptor signal transmission domain; (c) providing a second genetic construct encoding the second peptide chain comprising at least a first domain, a second domain, a variable region of a T cell receptor chain or a portion thereof, and an immunoreceptor signal transmission domain; (d) introducing the first and second genetic constructs into the cell; and (e) allowing the constructs to be expressed in the cell; wherein the first domain from the first peptide chain is able to form together with one of the domains from the second peptide chain a first antigen binding site, and wherein the second domain from the first peptide chain is able to form together with the other domain from the second peptide chain a second antigen binding site. In one embodiment of the methods of the invention, expression of the antigen receptor is at the cell surface. In one embodiment of the methods of the invention, the first peptide chain and the second peptide chain are provided on a single genetic construct. In one embodiment of the methods of the invention, the cell is a human cell. In one embodiment of the methods of the invention, the cell is an immune effector cell such as a T cell. In one embodiment of the methods of the invention, the genetic constructs comprise DNA and/or RNA. Further embodiments of the methods of the invention are as described herein for the antigen receptors of the invention.

In one aspect, the present invention relates to a recombinant cell, in particular an immune effector cell such as a T cell, produced by the methods of the invention for producing a cell expressing an antigen receptor. Further embodiments of the recombinant cell of the invention are as described herein for the antigen receptors of the invention or the methods of the invention for producing a cell expressing an antigen receptor.

In one aspect, the present invention relates to a nucleic acid such as DNA or RNA encoding the first peptide chain, the second peptide chain or both the first and second peptide chains of an antigen receptor of the invention or encoding a peptide chain of the invention. Further embodiments of the nucleic acid of the invention are as described herein for the antigen receptors of the invention or the peptide chains of the invention.

The present invention generally embraces the treatment of diseases by targeting cells expressing one or more antigens on the cell surface such as diseased cells expressing one or more disease-specific antigens on the cell surface, in particular cancer cells expressing one or more tumor antigens on the cell surface using antigen receptors of the invention. The methods provide for the selective eradication of cells that express on their surface one or more antigens, thereby minimizing adverse effects to normal cells not expressing the antigen(s). In one embodiment, T cells genetically modified to express an antigen receptor of the invention targeting the cells through binding to the antigen(s) are administered. T cells are able to recognize diseased cells expressing the antigen(s) on the cell surface, resulting in the eradication of diseased cells. In one embodiment, the target cell population or target tissue is tumor cells or tumor tissue.

In one aspect, the present invention relates to a pharmaceutical composition comprising the antigen receptor of the invention, the recombinant cell of the invention, or the nucleic acid of the invention; and a pharmaceutically acceptable carrier. The pharmaceutical composition of the invention may be used as a medicament, in particular in the treatment of a disease such as cancer characterized by expression of one or more antigens which are bound by the antigen receptor of the invention such as one or more tumor antigens.

In one aspect, the present invention relates to a method of treating a disease such as cancer comprising administering to a subject a therapeutically effective amount of the pharmaceutical composition of the invention, wherein the disease is characterized by expression of at least one antigen such as a tumor antigen which is bound by the antigen receptor.

In one aspect, the present invention relates to a method of treating a subject having a disease, disorder or condition associated with expression or elevated expression of at least one antigen, the method comprising administering to the subject T cells genetically modified to express an antigen receptor of the invention targeted to the at least one antigen. In one embodiment, the disease, disorder or condition is cancer. In one embodiment, the T cells may be autologous, allogeneic or syngeneic to the subject.

In one embodiment of the invention, the antigen receptor binds to only one antigen (e.g. by being monospecific and recognizing the same epitope or by being bispecific or multispecific and recognizing different epitopes on the same antigen) or binds to different antigens, in particular two different antigens.

In one embodiment of all aspects of the invention, the method of treating further comprises obtaining a sample of cells from a subject, the sample comprising T cells or T cell progenitors, and transfecting the cells with a nucleic acid encoding the antigen receptor of the invention to provide T cells genetically modified to express the antigen receptor. In one embodiment of all aspects of the invention, the T cells genetically modified to express the antigen receptor are stably or transiently transfected with nucleic acid encoding the antigen receptor. Thus, the nucleic acid encoding the antigen receptor is integrated or not integrated into the genome of the T cells. In one embodiment of all aspects of the invention, the T cells and/or the sample of cells are from the subject to which the T cells genetically modified to express the antigen receptor are administered. In one embodiment of all aspects of the invention, the T cells and/or the sample of cells are from a mammal which is different to the mammal to which the T cells genetically modified to express the antigen receptor are administered.

In one embodiment of all aspects of the invention, the T cells genetically modified to express the antigen receptor are inactivated for expression of an endogenous T cell receptor and/or endogenous HLA.

In one embodiment of all aspects of the invention, an antigen is expressed in a diseased cell such as a cancer cell. In one embodiment, an antigen is expressed on the surface of a diseased cell such as a cancer cell. In one embodiment, an antigen receptor binds to an extracellular domain or to an epitope in an extracellular domain of an antigen. In one embodiment, an antigen receptor binds to native epitopes of an antigen present on the surface of living cells. In one embodiment of all aspects of the invention, the antigen is a tumor antigen. In one embodiment of all aspects of the invention, the antigen is selected from the group consisting of claudins, such as claudin 6 and claudin 18.2, CD19, CD20, CD22, CD33, CD123, mesothelin, CEA, c-Met, PSMA, GD-2, and NY-ESO-1. In one embodiment of all aspects of the invention, the antigen is a pathogen antigen. The pathogen may be a fungal, viral, or bacterial pathogen. In one embodiment of all aspects of the invention, expression of the antigen is at the cell surface. In one embodiment an antigen is a claudin, in particular claudin 6 or claudin 18.2, and said antigen receptor binds to the first extracellular loop of said claudin. In one embodiment, binding of said antigen receptor when expressed by T cells and/or present on T cells to an antigen present on cells results in immune effector functions of said T cells such as the release of cytokines. In one embodiment, binding of said antigen receptor when expressed by T cells and/or present on T cells to an antigen present on cells such as antigen presenting cells results in stimulation, priming and/or expansion of said T cells. In one embodiment, binding of said antigen receptor when expressed by T cells and/or present on T cells to an antigen present on diseased cells such as cancer cells results in cytolysis and/or apoptosis of the diseased cells, wherein said T cells preferably release cytotoxic factors, e.g. perforins and granzymes.

In one embodiment of all aspects of the invention, the domains of an antigen receptor forming antigen binding sites are comprised by an ectodomain of the antigen receptor. In one embodiment of all aspects of the invention, an antigen receptor of the invention comprises a transmembrane domain. In one embodiment, the transmembrane domain is a hydrophobic alpha helix that spans the membrane.

In one embodiment of all aspects of the invention, an antigen receptor of the invention comprises a signal peptide which directs the nascent protein into the endoplasmic reticulum. In one embodiment, the signal peptide precedes the domains forming antigen binding sites.

In one embodiment of all aspects of the invention, an antigen receptor of the invention is preferably specific for the antigen to which it is targeted, in particular when present on the surface of a cell such as a diseased cell or an antigen-presenting cell.

In one embodiment of all aspects of the invention, an antigen receptor of the invention may be expressed by and/or present on the surface of an immunoreactive cell, such as a T cell, preferably a cytotoxic T cell. In one embodiment, the T cell is reactive with the antigen(s) to which the an antigen receptor of the invention is targeted.

In a further aspect, the invention provides the agents and compositions described herein for use in the methods described herein.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., Molecular Cloning: A Laboratory Manual, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "immune response" refers to an integrated bodily response to an antigen and preferably refers to a cellular immune response or a cellular as well as a humoral immune response. The immune response may be protective/preventive/prophylactic and/or therapeutic.

"Providing an immune response" may mean that there was no immune response against a particular target antigen, target cell and/or target tissue before providing an immune response, but it may also mean that there was a certain level of immune response against a particular target antigen, target cell and/or target tissue before providing an immune response and after providing an immune response said immune response is enhanced. Thus, "providing an immune response" includes "inducing an immune response" and "enhancing an immune response". Preferably, after providing an immune response in a subject, said subject is protected from developing a disease such as a cancer disease or the disease condition is ameliorated by providing an immune response. For example, an immune response against a tumor antigen may be provided in a patient having a cancer disease or in a subject being at risk of developing a cancer disease. Providing an immune response in this case may mean that the disease condition of the subject is ameliorated, that the subject does not develop metastases, or that the subject being at risk of developing a cancer disease does not develop a cancer disease.

"Cell-mediated immunity" or "cellular immunity", or similar terms are meant to include a cellular response directed to cells characterized by expression of an antigen, in particular characterized by presentation of an antigen with class I or class II MHC. The cellular response relates to cells called T cells or T-lymphocytes which act as either "helpers" or "killers". The helper T cells (also termed CD4$^+$ T cells) play a central role by regulating the immune response and the killer cells (also termed cytotoxic T cells, cytolytic T cells, CD8$^+$ T cells or CTLs) kill diseased cells such as cancer cells, preventing the production of more diseased cells.

The term "antigen" relates to an agent comprising an epitope against which an immune response is to be generated and/or is directed. Preferably, an antigen in the context of the present invention is a molecule which, optionally after processing, induces an immune reaction, which is preferably specific for the antigen or cells expressing the antigen, preferably on the cell surface. The term "antigen" includes in particular proteins and peptides. An antigen is preferably a product which corresponds to or is derived from a naturally occurring antigen. Such naturally occurring antigens may include or may be derived from allergens, viruses, bacteria, fungi, parasites and other infectious agents and pathogens or an antigen may also be a tumor antigen. According to the present invention, an antigen may correspond to a naturally occurring product, for example, a viral protein, or a part thereof.

The term "pathogen" relates to pathogenic microorganisms and comprises viruses, bacteria, fungi, unicellular organisms, and parasites. Examples for pathogenic viruses are human immunodeficiency virus (HIV), cytomegalovirus (CMV), herpes virus (HSV), hepatitis A-virus (HAV), HBV, HCV, papilloma virus, and human T-lymphotrophic virus (HTLV). Unicellular organisms comprise plasmodia, trypanosomes, amoeba, etc.

In a preferred embodiment, an antigen is a disease-specific antigen or disease-associated antigen. The term "disease-specific antigen" or "disease-associated antigen" refers to all antigens that are of pathological significance. In one particularly preferred embodiment, the antigen is present in diseased cells, tissues and/or organs while it is not present or present in a reduced amount in healthy cells, tissues and/or organs and, thus, can be used for targeting diseased cells, tissues and/or organs, e.g. by T cells carrying an antigen receptor targeted to the antigen. In one embodiment, a disease-specific antigen or disease-associated antigen is present on the surface of a diseased cell.

In a preferred embodiment, an antigen is a tumor antigen or tumor-associated antigen, i.e., a constituent of cancer cells which may be derived from the cytoplasm, the cell surface and the cell nucleus, in particular those antigens which are produced, preferably in large quantity, as surface antigens on cancer cells.

In the context of the present invention, the term "tumor antigen" or "tumor-associated antigen" relates to proteins that are under normal conditions specifically expressed in a limited number of tissues and/or organs or in a specific developmental stages, for example, the tumor antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor antigen is preferably associated with the cell surface of a cancer cell and is preferably not or only rarely expressed in normal tissues. Preferably, the tumor antigen or the aberrant expression of the tumor antigen identifies cancer cells. In the context of the present invention, the tumor antigen that is expressed by a cancer cell in a subject, e.g., a patient suffering from a cancer disease, is preferably a self-protein in said subject. In preferred embodiments, the tumor antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor antigen is identical between the tumor antigen which is expressed in normal tissues and the tumor antigen which is expressed in cancer tissues.

Examples for tumor antigens that may be useful in the present invention are p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pml/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT. Particularly preferred tumor antigens include CLAUDIN-18.2 (CLDN18.2) and CLAUDIN-6 (CLDN6).

The term "CLDN" or simply "Cl" as used herein means claudin and includes CLDN6 and CLDN18.2. Preferably, a claudin is a human claudin. Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop, termed EC1 or ECL1, consists on average of 53 amino acids, and the second extracellular loop, termed EC2 or ECL2, consists of around 24 amino acids. Cell surface proteins of the claudin family are expressed in tumors of various origins, and are particularly suited as target structures in connection with targeted cancer immunotherapy due to their selective expression (no expression in a toxicity relevant normal tissue) and localization to the plasma membrane.

CLDN6 and CLDN18.2 have been identified as differentially expressed in tumor tissues, with the only normal tissue expressing CLDN18.2 being stomach (differentiated epithelial cells of the gastric mucosa) and the only normal tissue expressing CLDN6 being placenta.

CLDN18.2 is expressed in cancers of various origins such as pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, pancreatic cancer, lung cancer such as non small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis. Antigen receptors targeting at least CLDN18.2 are useful in treating such cancer diseases.

CLDN6 has been found to be expressed, for example, in ovarian cancer, lung cancer, gastric cancer, breast cancer, hepatic cancer, pancreatic cancer, skin cancer, melanomas, head neck cancer, sarcomas, bile duct cancer, renal cell cancer, and urinary bladder cancer. CLDN6 is a particularly preferred target for the prevention and/or treatment of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof. Antigen receptors targeting at least CLDN6 are useful in treating such cancer diseases.

In the context of the embodiments of the present invention, an antigen is preferably present on the surface of a cell, preferably an antigen presenting cell or diseased cell. According to the invention, an antigen if bound by an antigen receptor is preferably able to induce, optionally in the presence of appropriate co-stimulatory signals, stimulation, priming and/or expansion of the T cell carrying the antigen receptor binding the antigen. Recognition of an antigen on the surface of a diseased cell may result in an immune reaction against the antigen (or cell expressing the antigen).

According to the various aspects of the invention, the aim is preferably to provide an immune response against diseased cells expressing an antigen such as cancer cells expressing an antigen such as a tumor antigen, in particular CLDN6 or CLDN18.2, and to treat a disease such as a cancer disease involving cells expressing an antigen such as a tumor antigen. Preferably the invention involves the administration of antigen receptor-engineered immune effector cells such as T cells targeted against diseased cells expressing an antigen. Cells expressing an antigen on the surface can be targeted by immune effector cells carrying an antigen receptor targeted to the antigen.

"Cell surface" is used in accordance with its normal meaning in the art, and thus includes the outside of the cell which is accessible to binding by proteins and other molecules. An antigen is expressed on the surface of cells if it is located at the surface of said cells and is accessible to binding by antigen-binding molecules such as antigen receptors or antigen-specific antibodies added to the cells. In one embodiment, an antigen expressed on the surface of cells is an integral membrane protein having an extracellular portion recognized by an antigen receptor. An antigen receptor is expressed on the surface of cells if it is located at the surface of said cells and is accessible to binding by e.g. antigen to which the antigen receptor is specific added to the cells. In one embodiment, an antigen receptor expressed on the surface of cells is an integral membrane protein having an extracellular portion recognizing antigen.

The term "extracellular portion" or "ectodomain" in the context of the present invention refers to a part of a molecule such as a protein that is facing the extracellular space of a cell and preferably is accessible from the outside of said cell, e.g., by binding molecules such as antibodies located outside the cell. Preferably, the term refers to one or more extracellular loops or domains or a fragment thereof.

The terms "portion" or "part" are used interchangeably herein and refer to a continuous or discontinuous element of a structure such as an amino acid sequence. The term "fragment" refers to a continuous element of a structure such as an amino acid sequence. A portion or part of a protein sequence preferably comprises at least 6, in particular at least 8, at least 12, at least 15, at least 20, at least 30, at least 50, or at least 100 consecutive and/or non-consecutive amino acids of the protein sequence. A fragment of a protein sequence preferably comprises at least 6, in particular at least 8, at least 12, at least 15, at least 20, at least 30, at least 50, or at least 100 consecutive amino acids of the protein sequence. A portion, part or fragment of a structure preferably comprises one or more functional properties, e.g. antigenic, immunologic and/or binding properties, of said structure. For example, a portion of a variable region of a T cell receptor chain is preferably able to form an antigen recognition site and bind antigen. Thus, if the variable region of a T cell receptor chain is V alpha, a portion thereof is preferably still able to interact with the corresponding V beta or a portion thereof to form a functional antigen recognition site. If the variable region of a T cell receptor chain is V beta, a portion thereof is preferably still able to interact with the corresponding V alpha or a portion thereof to form a functional antigen recognition site. Similarly, a portion of a constant region of a T cell receptor chain is preferably able to perform its signal transmission function.

According to the invention, an antigen is not (substantially) expressed in a cell if the level of expression is below the detection limit and/or if the level of expression is too low to allow binding by antigen-specific antibodies added to the cell. According to the invention, an antigen is expressed in a cell if the level of expression is above the detection limit and/or if the level of expression is high enough to allow binding by antigen-specific antibodies added to the cell. Preferably, an antigen expressed in a cell is expressed or exposed, i.e. is present, on the surface of said cell and, thus, available for binding by antigen-specific molecules such as antibodies or antigen receptors added to the cell.

"Target cell" shall mean a cell which is a target for an immune response such as a cellular immune response. Target cells include any undesirable cell such as a cancer cell. In preferred embodiments, the target cell is a cell expressing a target antigen, in particular a disease-specific antigen, which preferably is present on the cell surface.

The term "epitope" refers to an antigenic determinant in a molecule such as an antigen, i.e., to a part in or fragment of the molecule that is recognized, i.e. bound, by the immune system, for example, that is recognized by an antibody or antigen receptor. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. Preferably an epitope is capable of eliciting an immune response against the antigen or a cell expressing the antigen. Preferably, the term relates to an immunogenic portion of an antigen. An epitope of a protein such as a tumor antigen preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, preferably antigen presenting cells to specific T cells.

An antigen-presenting cell (APC) is a cell that displays antigen in the context of major histocompatibility complex (MHC) on its surface. T cells may recognize this complex using their T cell receptor (TCR). Antigen-presenting cells process antigens and present them to T cells. According to the invention, the term "antigen-presenting cell" includes professional antigen-presenting cells and non-professional antigen-presenting cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells. The main types of professional antigen-presenting cells are dendritic cells, which have the broadest range of antigen presentation, and are probably the most important antigen-presenting cells, macrophages, B-cells, and certain activated epithelial cells.

Non-professional antigen-presenting cells do not constitutively express the MHC class II proteins required for interaction with naive T cells; these are expressed only upon stimulation of the non-professional antigen-presenting cells by certain cytokines such as IFNγ.

Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity. Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFa to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells. Dendritic cells are conveniently categorized as "immature" and "mature" cells, which can be used as a simple way to discriminate between two well characterized phenotypes. However, this nomenclature should not be construed to exclude all possible intermediate stages of differentiation. Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e. g. CD54 and CD11) and costimulatory molecules (e. g., CD40, CD80, CD86 and 4-1 BB). Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

The term "immunogenicity" relates to the relative efficiency of an antigen to induce an immune reaction.

The term "immune effector functions" in the context of the present invention includes any functions mediated by components of the immune system that result, for example, in the killing of diseased cells such as tumor cells, or in the inhibition of tumor growth and/or inhibition of tumor development, including inhibition of tumor dissemination and metastasis. Preferably, the immune effector functions in the context of the present invention are T cell mediated effector functions. Such functions comprise in the case of a helper T cell (CD4$^+$ T cell) the release of cytokines such as Interleukin-2 and/or the activation of CD8$^+$ lymphocytes (CTLs) and/or B-cells, and in the case of CTL the elimination of cells, i.e., cells characterized by expression of an antigen, for example, via apoptosis or perforin-mediated cell lysis, production of cytokines such as IFN-γ and TNF-α, and specific cytolytic killing of antigen expressing target cells.

The term "immunoreactive cell" or "immune effector cell" in the context of the present invention relates to a cell which exerts effector functions during an immune reaction. An "immunoreactive cell" preferably is capable of binding an antigen such as an antigen expressed on the surface of a cell and mediating an immune response. For example, such cells secrete cytokines and/or chemokines, kill microbes, secrete antibodies, recognize infected or cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells. Preferably, in the context of the present invention, "immunoreactive cells" are T cells, preferably $CD4^+$ and/or $CD8^+$ T cells. According to the invention, the term "immunoreactive cell" also includes a cell which can mature into an immune cell (such as T cell, in particular T helper cell, or cytolytic T cell) with suitable stimulation. Immunoreactive cells comprise $CD34^+$ hematopoietic stem cells, immature and mature T cells and immature and mature B cells. The differentiation of T cell precursors into a cytolytic T cell, when exposed to an antigen, is similar to clonal selection of the immune system.

Preferably, an "immunoreactive cell" or "immune effector cell" recognizes an antigen with some degree of specificity, in particular if present on the surface of antigen presenting cells or diseased cells such as cancer cells. Preferably, said recognition enables the cell that recognizes an antigen to be responsive or reactive. If the cell is a helper T cell ($CD4^+$ T cell) such responsiveness or reactivity may involve the release of cytokines and/or the activation of $CD8^+$ lymphocytes (CTLs) and/or B-cells. If the cell is a CTL such responsiveness or reactivity may involve the elimination of cells, i.e., cells characterized by expression of an antigen, for example, via apoptosis or perforin-mediated cell lysis. According to the invention, CTL responsiveness may include sustained calcium flux, cell division, production of cytokines such as IFN-$\gamma$ and TNF-$\alpha$, up-regulation of activation markers such as CD44 and CD69, and specific cytolytic killing of antigen expressing target cells. CTL responsiveness may also be determined using an artificial reporter that accurately indicates CTL responsiveness. Such CTL that recognizes an antigen and are responsive or reactive are also termed "antigen-responsive CTL" herein.

A "lymphoid cell" is a cell which, optionally after suitable modification, e.g. after transfer of a T cell receptor or antigen receptor, is capable of producing an immune response such as a cellular immune response, or a precursor cell of such cell, and includes lymphocytes, preferably T lymphocytes, lymphoblasts, and plasma cells. A lymphoid cell may be an immunoreactive cell or immune effector cell as described herein. A preferred lymphoid cell is a T cell which can be modified to express a T cell receptor or antigen receptor on the cell surface. In one embodiment, the lymphoid cell lacks endogenous expression of a T cell receptor.

The terms "T cell" and "T lymphocyte" are used interchangeably herein and include T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptors (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCR$\alpha$ and TCR$\beta$) genes and are called $\alpha$- and $\beta$-TCR chains. $\gamma\delta$ T cells (gamma delta T cells) represent a small subset of T cells that possess a distinct T cell receptor (TCR) on their surface. However, in $\gamma\delta$ T cells, the TCR is made up of one $\gamma$-chain and one $\delta$-chain. This group of T cells is much less common (2% of total T cells) than the $\alpha\beta$ T cells.

Each chain of a T cell receptor is composed of two extracellular domains: variable (V) region and a constant (C) region. The constant region is proximal to the cell membrane, followed by a transmembrane region and a short cytoplasmic tail, while the variable region binds to the peptide/MHC complex. For the purpose of the present invention, the term "constant region of a T cell receptor chain or a portion thereof" also includes embodiments wherein the constant region of a T cell receptor chain is (from N terminus to C terminus) followed by a transmembrane region and a cytoplasmic tail, such as a transmembrane region and a cytoplasmic tail which are naturally linked to the constant region of a T cell receptor chain.

All T cells originate from hematopoietic stem cells in the bone marrow. Hematopoietic progenitors derived from hematopoietic stem cells populate the thymus and expand by cell division to generate a large population of immature thymocytes. The earliest thymocytes express neither CD4 nor CD8, and are therefore classed as double-negative (CD4−CD8−) cells. As they progress through their development they become double-positive thymocytes (CD4+CD8+), and finally mature to single-positive (CD4+CD8− or CD4−CD8+) thymocytes that are then released from the thymus to peripheral tissues.

T cells may generally be prepared in vitro or ex vivo, using standard procedures. For example, T cells may be isolated from bone marrow, peripheral blood or a fraction of bone marrow or peripheral blood of a mammal, such as a patient, using a commercially available cell separation system. Alternatively, T cells may be derived from related or unrelated humans, non-human animals, cell lines or cultures. A sample comprising T cells may, for example, be peripheral blood mononuclear cells (PBMC).

The T cells to be used according to the invention may express an endogenous T cell receptor or may lack expression of an endogenous T cell receptor.

Nucleic acids such as RNA encoding an antigen receptor may be introduced into T cells or other cells with lytic potential, in particular lymphoid cells.

The term "antigen receptor targeted to an antigen" or similar terms relate to an antigen receptor which when present on an immune effector cell such as a T cell recognizes the antigen such as on the surface of antigen presenting cells or diseased cells such as cancer cells, such that the immune effector cell is stimulated, primed and/or expanded or exerts effector functions of immune effector cells as described above.

The term "antigen-specific T cell" or similar terms relate to a T cell which, in particular when provided with an antigen receptor, recognizes the antigen to which the antigen receptor is targeted such as on the surface of antigen presenting cells or diseased cells such as cancer cells and preferably exerts effector functions of T cells as described above. T cells and other lymphoid cells are considered to be specific for antigen if the cells kill target cells expressing an antigen. T cell specificity may be evaluated using any of a variety of standard techniques, for example, within a chromium release assay or proliferation assay. Alternatively, synthesis of lymphokines (such as interferon-γ) can be measured.

The term "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self antigens (peptide fragments from the cell itself) and nonself antigens (e.g., fragments of invading microorganisms) to a T cell.

According to the invention the term "antigen receptor" includes engineered receptors, which confer an arbitrary specificity such as the specificity of a monoclonal antibody onto an immune effector cell such as a T cell. In this way, a large number of antigen-specific T cells can be generated for adoptive cell transfer. Thus, an antigen receptor according to the invention may be present on T cells, e.g. instead of or in addition to the T cell's own T cell receptor. Such T cells do not necessarily require processing and presentation of an antigen for recognition of the target cell but rather may recognize preferably with specificity any antigen present on a target cell. Preferably, said antigen receptor is expressed on the surface of the cells. For the purpose of the present invention T cells comprising an antigen receptor are comprised by the term "T cell" as used herein. Specifically, according to the invention, the term "antigen receptor" includes artificial receptors comprising a single molecule or a complex of molecules which recognize, i.e. bind to, a target structure (e.g. an antigen) on a target cell such as a cancer cell (e.g. by binding of an antigen binding site or antigen binding domain to an antigen expressed on the surface of the target cell) and may confer specificity onto an immune effector cell such as a T cell expressing said antigen receptor on the cell surface. Preferably, recognition of the target structure by an antigen receptor results in activation of an immune effector cell expressing said antigen receptor. An antigen receptor may comprise one or more protein units said protein units comprising one or more domains as described herein. The term "antigen receptor" preferably does not include T cell receptors. According to the invention the term "antigen receptor" is preferably synonymous with the terms "chimeric antigen receptor (CAR)", "chimeric T cell receptor" and "artificial T cell receptor".

According to the invention, antigen can be recognized by an antigen receptor through any antigen recognition domains (herein also referred to simply as "domains") able to form an antigen binding site such as through antigen-binding portions of antibodies and T cell receptors which may reside on different peptide chains. In one embodiment, the two domains forming an antigen binding site are derived from an immunoglobulin. In another embodiment, the two domains forming an antigen binding site are derived from a T cell receptor. Particularly preferred are antibody variable domains, such as single-chain variable fragments (scFv) derived from monoclonal antibodies and T cell receptor variable domains, in particular TCR alpha and beta single chains. In fact almost anything that binds a given target with high affinity can be used as an antigen recognition domain.

In one embodiment, an antigen receptor of the invention comprises at least four immunoglobulin variable domains forming at least two binding sites, wherein the two binding sites may bind to the same or different epitopes, which epitopes may be located on the same or different antigens. In one embodiment the antigen receptor comprises a variable domain (or region) of a heavy chain of an immunoglobulin (VH) with a specificity for a first epitope (VH(1)), a variable domain (or region) of a light chain of an immunoglobulin (VL) with a specificity for a first epitope (VL(1)), a variable domain (or region) of a heavy chain of an immunoglobulin (VH) with a specificity for a second epitope (VH(2)), and a variable domain (or region) of a light chain of an immunoglobulin (VL) with a specificity for a second epitope (VL(2)), which first and second epitopes may be the same or different and may be located on the same or different antigens. In one embodiment, VH(1) is able to interact and form an antigen binding site with VL(1) and VH(2) is able to interact and form an antigen binding site with VL(2), while VH(1) is not able to interact and form an antigen binding site with VL(2) and VH(2) is not able to interact and form an antigen binding site with VL(1). In another embodiment, however, VH(1) is able to interact and form an antigen binding site with VL(1) as well as VL(2) and VH(2) is able to interact and form an antigen binding site with VL(2) as well as VL(1). In the latter embodiment, VH(1) and VH(2) may be identical or at least derived from the same immunoglobulin and VL(1) and VL(2) may be identical or at least derived from the same immunoglobulin.

In one aspect, the invention relates to an antigen receptor, also termed combinatory antigen receptor herein, which receptor comprises a first peptide chain and a second peptide chain, wherein the first peptide chain comprises a first domain, a second domain, a variable region of a T cell receptor chain or a portion thereof, and an immunoreceptor signal transmission domain; the second peptide chain comprises a first domain, a second domain, a variable region of a T cell receptor chain or a portion thereof, and an immunoreceptor signal transmission domain; wherein the first domain from the first peptide chain forms together with one of the domains from the second peptide chain a first antigen binding site, and wherein the second domain from the first peptide chain forms together with the other domain from the second peptide chain a second antigen binding site.

In one embodiment, the combinatory antigen receptor of the invention comprises a heavy chain variable domain connected to a light chain variable domain on each of both peptide chains wherein formation of two antigen binding sites takes place through interaction between a heavy chain variable domain and a light chain variable domain on different peptide chains. In one embodiment, the combinatory antigen receptor of the invention comprises two peptide chains, wherein one peptide chain comprises VL(1) and VH(2) and the other polypeptide chain comprises VH(1) and VL(2). In another embodiment, the combinatory antigen receptor of the invention comprises a heavy chain variable domain connected to a heavy chain variable domain on one peptide chain and a light chain variable domain connected to a light chain variable domain on the other peptide chain wherein formation of two antigen binding sites takes place through interaction between a heavy chain variable domain and a light chain variable domain on different peptide chains. In one embodiment, the combinatory antigen receptor of the invention comprises two peptide chains, wherein one peptide chain comprises VH(1) and VH(2) and the other peptide chain comprises VL(1) and VL(2).

In one embodiment, the combinatory antigen receptor of the invention comprises a first peptide chain wherein the heavy chain variable region (VH) and the light chain variable region (VL) are preferably arranged, from N-terminus to C-terminus, in the order VH(1)-VL(2) and a second peptide chain wherein the heavy chain variable region (VH) and the light chain variable region (VL) are preferably arranged, from N-terminus to C-terminus, in the order VL(1)-VH(2). The variable region of a T cell receptor chain or a portion thereof, and the immunoreceptor signal transmission domain are preferably located C-terminal to the arrangement of variable regions. The variable region of a T cell receptor chain or a portion thereof, and the immunoreceptor signal transmission domain preferably comprises a variable region of a T cell receptor alpha chain or a portion thereof and a constant region of a T cell receptor alpha chain or a portion thereof located on one of the peptide chains, and a variable region of a T cell receptor beta chain or a portion thereof and a constant region of a T cell receptor beta chain located on the other of the peptide chains. In one embodiment, the variable region of a T cell receptor alpha chain or a portion thereof and the constant region of a T cell receptor alpha chain or a portion thereof comprises the alpha chain of a T cell receptor. In one embodiment, the variable region of a T cell receptor beta chain or a portion thereof and the constant region of a T cell receptor beta chain or a portion thereof comprises the beta chain of a T cell receptor. The alpha chain of a T cell receptor and the beta chain of a T cell receptor are preferably from the same T cell receptor.

In one embodiment, the combinatory antigen receptor of the invention comprises a first peptide chain wherein the heavy chain variable region (VH) and the light chain variable region (VL) are preferably arranged, from N-terminus to C-terminus, in the order VH(1)-VH(2) and a second peptide chain wherein the heavy chain variable region (VH) and the light chain variable region (VL) are preferably arranged, from N-terminus to C-terminus, in the order VL(1)-VL(2). The variable region of a T cell receptor chain or a portion thereof, and the immunoreceptor signal transmission domain are preferably located C-terminal to the arrangement of variable regions. The variable region of a T cell receptor chain or a portion thereof, and the immunoreceptor signal transmission domain preferably comprises a variable region of a T cell receptor alpha chain or a portion thereof and a constant region of a T cell receptor alpha chain or a portion thereof located on one of the peptide chains, and a variable region of a T cell receptor beta chain or a portion thereof and a constant region of a T cell receptor beta chain or a portion thereof located on the other of the peptide chains. In one embodiment, the variable region of a T cell receptor alpha chain or a portion thereof and the constant region of a T cell receptor alpha chain or a portion thereof comprises the alpha chain of a T cell receptor. In one embodiment, the variable region of a T cell receptor beta chain or a portion thereof and the constant region of a T cell receptor beta chain or a portion thereof comprises the beta chain of a T cell receptor. The alpha chain of a T cell receptor and the beta chain of a T cell receptor are preferably from the same T cell receptor.

Antigen receptors of the invention have at least two antigen binding sites and thus, are at least bivalent. As noted above, the binding sites of the antigen receptors of the invention may bind to the same or different epitopes, which epitopes may be located on the same or different antigens. If the binding sites bind to the same epitopes, in particular on the same antigen, the two binding sites may be identical or essentially identical and/or may be formed by identical or essentially identical domains, wherein such identical or essentially identical domains may be derived, for example, from the same immunoglobulin. If the binding sites bind to different epitopes, either on the same or different antigens, the two binding sites are different and are formed by different domains, wherein such different domains may be derived from different immunoglobulins. In the case of such different domains it is preferred that the domains having different epitope specificities do not interact or do not substantially interact with each other, i.e. VH(1) is not able to interact and form an antigen binding site with VL(2) and VH(2) is not able to interact and form an antigen binding site with VL(1). Consequently, VH(1) interacts and forms an antigen binding site with VL(1) and VH(2) interact and forms an antigen binding site with VL(2). If a combinatory antigen receptor of the invention comprises two peptide chains, wherein one peptide chain comprises VH(1) and VL(2) and the other peptide chain comprises VH(2) and VL(1), this results in the peptide chains not being able to form antigen binding sites through intramolecular interaction of domains.

The two domains of an antigen receptor of the invention forming an antigen binding site also can be derived from a T cell receptor and can be fragments or portions thereof that maintain antigen-specific binding, in particular binding to the peptide-MHC complex, such as the variable regions of a T cell receptor.

According to the invention, the term "variable region of a T cell receptor" relates to the variable domains of the TCR chains. The variable region of both the TCR α-chain and β-chain have three hypervariable or complementarity determining regions (CDRs), whereas the variable region of the β-chain has an additional area of hypervariability (HV4) that does not normally contact antigen and therefore is not considered a CDR. CDR3 is the main CDR responsible for recognizing processed antigen, although CDR1 of the α-chain has also been shown to interact with the N-terminal part of the antigenic peptide, whereas CDR1 of the β-chain interacts with the C-terminal part of the peptide. CDR2 is thought to recognize the MHC. CDR4 of the β-chain is not thought to participate in antigen recognition, but has been shown to interact with superantigens.

The above disclosure relating to immunoglobulin variable domains applies in a corresponding manner to T cell receptor variable domains. An antigen receptor of the invention instead of a variable domain of a heavy chain of an immunoglobulin (VH) with a specificity for a first epitope (VH(1)) and a variable domain of a light chain of an immunoglobulin (VL) with a specificity for a first epitope (VL(1)) may comprise a variable domain of a TCR α-chain of a TCR with a specificity for a first epitope and a variable domain of a TCR β-chain of a TCR with a specificity for a first epitope. Alternatively or additionally, an antigen receptor of the invention instead of a variable domain of a heavy chain of an immunoglobulin (VH) with a specificity for a second epitope (VH(2)), and a variable domain of a light chain of an immunoglobulin (VL) with a specificity for a second epitope (VL(2)) may comprise a variable domain of a TCR α-chain of a TCR with a specificity for a second epitope and a variable domain of a TCR β-chain of a TCR with a specificity for a second epitope.

Since each antigen binding site is formed from two domains, each domain can comprise a portion or a fragment of an immunoglobulin or T cell receptor, respectively. The individual portion or fragment alone may not be able to bind the antigen but when the two individual portions or fragments associate they together form or recreate the antigen binding structure of the original immunoglobulin or T cell receptor and, thus, are able to bind the same antigen, preferably with the same affinity.

Following antigen recognition, receptors preferably cluster and a signal is transmitted to the cell. In this respect, an "immunoreceptor signal transmission domain" or "T cell signaling domain" is a domain which is involved in transmitting an activation signal to the T cell after antigen is bound. Such signal transmission may be enabled by the antigen receptors of the invention comprising a constant or invariant region of a T cell receptor chain or a constant or invariant region of an immune cell Fc receptor chain or a portion of the constant or invariant region, such as a constant region of a T cell receptor alpha chain or a portion thereof, on one peptide chain and comprising the corresponding constant or invariant region of a T cell receptor chain or corresponding constant or invariant region of an immune cell Fc receptor chain or a portion of the constant or invariant region, such as a constant region of a T cell receptor beta chain or a portion thereof, on the other peptide chain. In this respect, the CD3 complex denotes an antigen that is expressed on mature human T cells, thymocytes and a subset of natural killer cells as part of the multimolecular T cell receptor (TCR) complex. The T cell co-receptor is a protein complex and is composed of four distinct chains. In mammals, the complex contains a CD3γ chain, a CD3δ chain, and two CD3ε chains. These chains associate with the T cell receptor (TCR) and the ζ-chain to generate an activation signal in T lymphocytes. The TCR, ζ-chain, and CD3 molecules together comprise the TCR complex. CD3 is responsible for the signal transduction of the TCR. As described by Lin and Weiss, Journal of Cell Science 114, 243-244 (2001), activation of the TCR complex by binding of MHC-presented specific antigen epitopes results in the phosphorylation of immunoreceptor tyrosine-based activation motifs (ITAMs) by Src family kinases, triggering recruitment of further kinases which results in T cell activation including $Ca^{2+}$ release. Clustering of CD3 on T cells, e.g. by immobilized anti-CD3-antibodies, leads to T cell activation similar to the engagement of the T cell receptor, but independent from its clone typical specificity.

The antigen receptor signal transmission domain preferably at a minimum serves to interact with the native cellular signal transduction complex, e.g., the CD3 complex, which is responsible for transmitting the signal of antigen binding to an antigen receptor into the cell, resulting in immune cell activation. The identity of the signal transmission domain is limited only in that it has the ability to interact with the native signal transduction complex to induce activation of the immune cell upon binding of the antigen to the antigen receptor.

Preferably, the signal transmission domain on one peptide chain will form a dimer with the signal transmission domain on the second chain, for example, through disulfide bridges. Preferred signal transmission domains can comprise a constant or invariant region of a T cell receptor chain or a constant or invariant region of an immune cell Fc receptor chain or a portion of the constant or invariant region. Preferred signal transmission domains can comprise the constant region of the alpha, beta, gamma or delta chains of a T cell receptor or portion thereof, as well as the D2 or D3 invariant regions of the constant domain of an immune cell Fc receptor or a portion thereof. In a preferred embodiment, the first peptide chain comprises a constant region of a T cell receptor alpha chain or a portion thereof and the second peptide chain comprises a constant region of a T cell receptor beta chain or a portion thereof. In this embodiment, the first peptide chain preferably comprises a variable region of a T cell receptor alpha chain or a portion thereof and the second peptide chain comprises a variable region of a T cell receptor beta chain or a portion thereof, wherein the variable regions are located at the N terminus of the constant regions. Alternatively, the first peptide chain comprises a constant region of a T cell receptor beta chain or a portion thereof and the second peptide chain comprises a constant region of a T cell receptor alpha chain or a portion thereof. In this embodiment, the first peptide chain preferably comprises a variable region of a T cell receptor beta chain or a portion thereof and the second peptide chain comprises a variable region of a T cell receptor alpha chain or a portion thereof, wherein the variable regions are located at the N terminus of the constant regions. In another embodiment, the first peptide chain comprises a constant region of a T cell receptor gamma chain or a portion thereof and the second peptide chain comprises a constant region of a T cell receptor delta chain or a portion thereof. In this embodiment, the first peptide chain preferably comprises a variable region of a T cell receptor gamma chain or a portion thereof and the second peptide chain comprises a variable region of a T cell receptor delta chain or a portion thereof, wherein the variable regions are located at the N terminus of the constant regions. Alternatively, the first peptide chain comprises a constant region of a T cell receptor delta chain or a portion thereof and the second peptide chain comprises a constant region of a T cell receptor gamma chain or a portion thereof. In this embodiment, the first peptide chain preferably comprises a variable region of a T cell receptor delta chain or a portion thereof and the second peptide chain comprises a variable region of a T cell receptor gamma chain or a portion thereof, wherein the variable regions are located at the N terminus of the constant regions. Optionally, the signal transmission domains, or the variable region of a T cell receptor chain or a portion thereof can be modified such that additional disulfide bonds between the chains are created, leading to more effective dimer formation and to greater stability of the dimer.

While not wanting to be limited to a particular mechanism of action, it is believed that the two peptide chains of the antigen receptor of the invention, when expressed on the surface of an immune cell, form a dimer due to interactions (e.g., disulfide bonding) at least between the individual immunoreceptor signal transmission domains on the two chains, as well as form a complex with the endogenous CD3 complex involved in physiological T cell receptor signal transduction. However, the invention may also include the direct fusion to CD3ζ or any other immune cell signaling domain (CD3, CD3 subunit FcγR) instead of TCR Cα and Cβ-domains. Upon antigen binding, it is believed that a signal is transmitted into the cell leading to the activation of the immune cell and to the generation of an antigen-specific immune response. Further, it is believed that inter-chain antigen binding provides for a more stable antigen-antigen receptor-endogenous CD3 signal transduction module, which greater stability in turn allows for a more effective stimulation of an antigen-specific immune response, as compared to monovalent receptors and bivalent receptors only capable of intra-chain antigen binding. This greater stability also is believed to allow for the option of using only human origin immunoreceptor signal transmission domains (e.g., minimal or no substitution of a human-derived amino acid sequence with an amino acid sequence derived from another species, such as mouse). Thus, any potential unwanted immune response against the antigen receptor itself can be avoided.

Antigen receptors according to the invention or peptide chains thereof may in addition to the domains forming the antigen binding sites, variable regions of a T cell receptor chain or a portion thereof, and immunoreceptor signal transmission domains including CD3ζ or any other immune cell signaling domain also comprise one or more co-stimulation domains. The co-stimulation domains serve to enhance the proliferation and survival of the T cells such as cytotoxic T cells upon binding of the antigen receptor to a targeted moiety. The identity of the co-stimulation domains is limited only in that they have the ability to enhance cellular proliferation and survival upon binding of the targeted moiety by the antigen receptor. Suitable co-stimulation domains include CD28, CD137 (4-1BB), a member of the tumor necrosis factor (TNF) receptor family, CD134 (OX40), a member of the TNFR-superfamily of receptors, and CD278 (ICOS), a CD28-superfamily co-stimulatory molecule expressed on activated T cells. The skilled person will understand that sequence variants of these noted co-stimulation domains can be used without adversely impacting the invention, where the variants have the same or similar activity as the domain on which they are modeled. Such variants will have at least about 80% sequence identity to the amino acid sequence of the domain from which they are derived. In some embodiments of the invention, the antigen receptor constructs or peptide chains thereof comprise two co-stimulation domains. While the particular combinations include all possible variations of the four noted domains, specific examples include CD28+CD137 (4-1BB) and CD28+CD134 (OX40).

The antigen receptors of the present invention or peptide chains thereof may comprise one or more co-stimulation domains, and immunoreceptor signal transmission domains, linked in a N-terminal to C-terminal direction. However, the antigen receptors of the present invention or peptide chains thereof are not limited to this arrangement and other arrangements are acceptable and include immunoreceptor signal transmission domains, and one or more co-stimulation domains.

It will be understood that because the domains forming the antigen binding sites must be free to bind antigen, the placement of these domains in the fusion protein will generally be such that display of the region on the exterior of the cell is achieved. In the same manner, because the co-stimulation domains, and immunoreceptor signal transmission domains serve to induce activity and proliferation of the T cells, the fusion protein will generally display these domains in the interior of the cell. The antigen receptors may include additional elements, such as a signal peptide to ensure proper export of the fusion protein to the cells surface, a transmembrane domain to ensure the fusion protein is maintained as an integral membrane protein, and a hinge domain (or spacer region) that imparts flexibility to the domains forming the antigen binding sites and allows strong binding to antigen.

Optionally, the antigen receptors of the invention can further comprise a linker, which linker can be an arbitrary amino acid sequence or other chemical compound useful as a spacer between amino acid sequences. The linker is generally designed to provide for flexibility and protease resistance.

For example, the linker can be between the first and second domains on the first peptide chain and/or between the first and second domains on the second peptide chain of a combinatory antigen receptor of the invention. Optionally, the linker can be present between the domains that form the antigen binding sites and the variable region of a T cell receptor chain or a portion thereof. Any type of linker known in the art that allows the domains to form an antigen binding site or does not interfere with antigen binding is encompassed by the invention. In specific embodiments, the linker can be an arbitrary amino acid sequence and can be at least 5, 10, 15, 20, 25 30, 35, 40, 45, 50, 55, 60, 65, 70, 75, 80, 85, 90, 95 or at least 100 amino acid residues in length. An amino acid linker is typically rich in glycine for flexibility, as well as serine and threonine for solubility. In one embodiment, the linker is one or more (1, 2, 3, 4, 5, 6, 7, 8 or 9) repeats of four glycine residues followed by a serine residue (Gly4Ser) (residues 1-5 of SEQ ID NO: 1). In certain embodiments, the linker can be a hinge region of an antibody or a fragment thereof.

The antigen receptor of the invention can further comprise another domain anchoring the antigen receptor on the membrane, such as a classical transmembrane domain. Preferably, the transmembrane domain is incorporated in or is a part of the signal transmission domain.

In other embodiments, antigen receptors or peptide chains of antigen receptors of the invention can further comprise other domains, such as additional domains involved in or enhancing antigen binding, signal sequences for membrane bound expression or for secretion, domains that provide improved dimerization, and a transmembrane domain, when not already a part of the immunoreceptor signal transmission domain. In certain embodiments, the transmembrane domain can be a hydrophobic alpha helix that spans the membrane.

Preferably, a signal sequence or signal peptide is a sequence or peptide that allows for sufficient passage through the secretory pathway and expression on the cell surface such that an antigen receptor, for example, may bind an antigen present in the extracellular environment. Preferably, the signal sequence or signal peptide is cleavable and is removed from the mature peptide chains. The signal sequence or signal peptide preferably is chosen with respect to the cell or organism wherein the peptide chains are produced in.

In a particular embodiment, a peptide chain of a combinatory antigen receptor of the invention can comprise the structure: NH2-signal peptide-first domain involved in antigen binding-optional linker-second domain involved in antigen binding-optional linker-variable region of a T cell receptor chain or a portion thereof-immunoreceptor signal transmission domain-COOH.

Exemplary antigen receptors of the invention, include but are not limited to those formed by the first and second peptide chains having the structures listed in the Table I below (VH being the variable region of a heavy chain of an immunoglobulin or a portion thereof; VL being the variable region of a light chain of an immunoglobulin or portion thereof; V1 and V2 being the variable regions of a T cell receptor chain or a portion thereof that will form a dimer with each other, C1 and C2 being the immunoreceptor signal transmission domains that will form a dimer with each other, e.g., the constant or invariant region of an immune cell Fc receptor chain, or the constant or invariant region of a T cell receptor chain, or a portion of the constant or invariant region). If C1 and C2 each are constant regions of a T cell receptor chain, V1 and C1 are preferably from the same T cell receptor chain and V2 and C2 are preferably from the same T cell receptor chain, the T cell receptor chains being preferably from the same T cell receptor. In particular, V1-C1 in one embodiment corresponds in essence to the sequence of a T cell receptor chain (TCR alpha or TCR beta) and V2-C2 corresponds in essence to the sequence of the complementary T cell receptor chain (TCR beta if V1-C1 is TCR alpha or TCR alpha if V1-C1 is TCR beta).

TABLE I

| First peptide chain | Second peptide chain |
| --- | --- |
| VH(1)-VL(2)-V1-C1 | VL(1)-VH(2)-V2-C2 |
| VH(1)-VH(2)-V1-C1 | VL(1)-VL(2)-V2-C2 |
| VH(1)-VH(2)-V1-C1 | VL(2)-VL(1)-V2-C2 |
| VH(1)-VL(2)-V1-C1 | VH(2)-VL(1)-V2-C2 |

As defined above, the antigen receptor comprises a variable domain of a heavy chain of an immunoglobulin (VH) with a specificity for a first epitope (VH(1)), a variable domain of a light chain of an immunoglobulin (VL) with a specificity for a first epitope (VL(1)), a variable domain of a heavy chain of an immunoglobulin (VH) with a specificity for a second epitope (VH(2)), and a variable domain of a light chain of an immunoglobulin (VL) with a specificity for a second epitope (VL(2)), which first and second epitopes may be the same or different and may be located on the same or different antigens. In one embodiment, VH(1) is able to interact and form an antigen binding site with VL(1) and VH(2) is able to interact and form an antigen binding site with VL(2), while VH(1) is not able to interact and form an antigen binding site with VL(2) and VH(2) is not able to interact and form an antigen binding site with VL(1). In another embodiment, however, VH(1) is able to interact and form an antigen binding site with VL(1) as well as VL(2) and VH(2) is able to interact and form an antigen binding site with VL(2) as well as VL(1). In the latter embodiment, VH(1) and VH(2) may be identical or at least derived from the same immunoglobulin and VL(1) and VL(2) may be identical or at least derived from the same immunoglobulin.

In specific embodiments, the V1 and V2 domains of the first and second peptide chains listed in Table 1 are the variable regions of the T cell receptor alpha and beta chains, respectively, or a portion thereof. In specific embodiments, the C1 and C2 domains of the first and second peptide chains listed in Table 1 are the constant regions of the T cell receptor alpha and beta chains, respectively, or a portion thereof.

In one embodiment, the V1 and C1 domains of the first peptide chain listed in Table 1 are the variable and constant regions of the T cell receptor alpha chain or a portion thereof. In this embodiment, the V2 and C2 domains of the second peptide chain listed in Table 1 are preferably the variable and constant regions of the T cell receptor beta chain or a portion thereof. In one embodiment, the V1 and C1 domains of the first peptide chain listed in Table 1 are the variable and constant regions of the T cell receptor beta chain or a portion thereof. In this embodiment, the V2 and C2 domains of the second peptide chain listed in Table 1 are preferably the variable and constant regions of the T cell receptor alpha chain or a portion thereof.

In a preferred embodiment, when the two domains on one peptide chain are both an immunoglobulin heavy chain variable region or a portion thereof and the two domains on the other chain are both an immunoglobulin light chain variable region or a portion thereof, a linker is present between the first and second domains on both peptide chains. The linker can be an arbitrary amino acid sequence between 10 and 25 amino acids in length, more preferably 15 amino acids in length. In a specific embodiment, the linker is 3 repeats of the 5-mer amino acid sequence (Gly4Ser)(SEQ ID NO: 1).

In certain embodiments of the invention, the amino acid sequences of the first and second peptide chains, such as those comprising one or more of the domains that form the antigen binding sites, the variable region of a T cell receptor chain or a portion thereof, or the immunoreceptor signal transmission domain, are of mammalian origin, preferably mouse origin, and more preferably human origin. In one embodiment, the amino acid sequences are of human origin but have been murinized by the substitution of one or more amino acids in the human sequence with the amino acid found in the corresponding position in the mouse sequence. Such substitution can provide for greater dimerization or stability or ability to transmit a signal into the cell upon antigen binding. In yet another embodiment, the amino acid sequences are of mouse origin and have been humanized.

According to the invention an antigen receptor may replace the function of a T cell receptor as described above and, in particular, may confer reactivity such as cytolytic activity to a cell such as a T cell as described above. However, in contrast to the binding of the T cell receptor to an antigen peptide-MHC complex as described above, an antigen receptor may in certain embodiments bind to an antigen, in particular when expressed on the cell surface.

The amino acid sequences of the peptide chains, including any of the domains or linkers, can be modified. For example, and as is appreciated by those skilled in the art, the sequences of the variable regions of antibodies and T cell receptors can be modified without losing the ability to bind to a target and consequently the amino acid sequence of the antigen binding sites can be similarly modified without losing the ability to bind a target. For example, the amino acid sequence of a domain forming an antigen binding site can be identical or highly homologous to the variable region of the antibody from which is was derived. By "highly homologous" it is contemplated that from 1 to 5, preferably from 1 to 4, such as 1 to 3 or 1 or 2 substitutions may be made. In one embodiment, a peptide chain may include natural amino acids and non-natural amino acids. In another embodiment, a peptide chain merely includes natural amino acids. The term "non-natural amino acid" refers to an amino acid having a structure different from those of the 20 natural amino acid species. Since non-natural amino acids have structures similar to those of natural amino acids, non-natural amino acids may be classified as derivatives or analogs of given natural amino acids.

In one embodiment, the amino acid sequence of one or more of the variable regions of T cell receptors or portions thereof, in particular those not forming the antigen binding sites, can be modified in order to eliminate (residual) binding to its antigen. In particular, such "silencing" modification can be effected by introducing one or more mutations into CDR3 of the variable region of TCR alpha and/or TCR beta.

The present invention also encompasses derivatives of the antigen receptors and peptide chains described herein. According to the invention, "derivatives" are modified forms of proteins and peptides. Such modifications include any chemical modification and comprise single or multiple substitutions, deletions and/or additions of any molecules associated with the antigen receptor or peptide chain, such as carbohydrates, lipids and/or proteins or peptides. In one embodiment, "derivatives" of proteins or peptides include those modified analogs resulting from glycosylation, acetylation, phosphorylation, amidation, palmitoylation, myristoylation, isoprenylation, lipidation, alkylation, derivatization, introduction of protective/blocking groups, proteolytic cleavage or binding to an antigen. The term "derivative" also extends to all functional chemical equivalents of said antigen receptors and peptide chains. Preferably, a modified antigen receptor or peptide chain thereof has increased binding or dimerization ability and/or increased immune activating ability.

The cells used in connection with the antigen receptor system of the present invention are preferably T cells, in particular cytotoxic lymphocytes, preferably selected from cytotoxic T cells, natural killer (NK) cells, and lymphokine-activated killer (LAK) cells. Upon activation, each of these cytotoxic lymphocytes triggers the destruction of target cells. For example, cytotoxic T cells trigger the destruction of target cells by either or both of the following means. First, upon activation T cells release cytotoxins such as perforin, granzymes, and granulysin. Perforin and granulysin create pores in the target cell, and granzymes enter the cell and trigger a caspase cascade in the cytoplasm that induces apoptosis (programmed cell death) of the cell. Second, apoptosis can be induced via Fas-Fas ligand interaction between the T cells and target cells. The cytotoxic lymphocytes will preferably be autologous cells, although heterologous cells or allogenic cells can be used.

The term "immunoglobulin" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Membrane bound immunoglobulins are also termed surface immunoglobulins or membrane immunoglobulins, which are generally part of the BCR. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the VL (variable light chain) domain, CL (constant light chain) domain, and the CH (constant heavy chain) domains $C_H1$, $C_H2$, $C_H3$, and $C_H4$. There are five types of mammalian immunoglobulin heavy chains, i.e., $\alpha$, $\delta$, $\varepsilon$, $\gamma$, and $\mu$ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

The term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies and chimeric antibodies. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

The antigen receptors described herein may comprise antigen-binding portions of one or more antibodies. The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')2 fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

A single-chain variable fragment (scFv) is a fusion protein of the variable regions of the heavy (VH) and light chains (VL) of immunoglobulins, connected with a linker peptide. The linker can either connect the N-terminus of the VH with the C-terminus of the VL, or vice versa. Divalent (or bivalent) single-chain variable fragments (di-scFvs, bi-scFvs) can be engineered by linking two scFvs. This can be done by producing a single peptide chain with two VH and two VL regions, yielding tandem scFvs.

The term "binding domain" or simply "domain" characterizes in connection with the present invention a structure, e.g. of an antibody, which binds to/interacts with a given target structure/antigen/epitope, optionally when interacting with another domain. Thus, these domains according to the invention designate an "antigen binding site".

Antibodies and derivatives of antibodies are useful for providing binding domains such as antibody fragments, in particular for providing VL and VH regions.

Binding domains for an antigen which may be present within an antigen receptor have the ability of binding to (targeting) an antigen, i.e. the ability of binding to (targeting) an epitope present in an antigen, preferably an epitope located within the extracellular domain of an antigen. Preferably, binding domains for an antigen are specific for the antigen. Preferably, binding domains for an antigen bind to the antigen expressed on the cell surface. In particular preferred embodiments, binding domains for an antigen bind to native epitopes of an antigen present on the surface of living cells.

All antibodies and derivatives of antibodies such as antibody fragments as described herein for the purposes of the invention are encompassed by the term "antibody".

Antibodies can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitonealy or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

The ability of antibodies and other binding agents to bind an antigen can be determined using standard binding assays (e.g., ELISA, Western Blot, Immunofluorescence and flow cytometric analysis).

The term "binding" according to the invention preferably relates to a specific binding.

According to the present invention, an agent such as an antigen receptor is capable of binding to (targeting) a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An agent is not (substantially) capable of binding to (targeting) a target if it has no significant affinity for said target and does not bind significantly, in particular does not bind detectably, to said target in standard assays. Preferably, the agent does not detectably bind to said target if present in a concentration of up to 2, preferably 10, more preferably 20, in particular 50 or 100 µg/ml or higher. Preferably, an agent has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the agent is capable of binding. For example, if the $K_D$ for binding of an agent to the target to which the agent is capable of binding is $10^{-7}$ M, the $K_D$ for binding to a target for which the agent has no significant affinity would be at least $10^{-6}$ M, $10^{-5}$ M, $10^{-4}$ M, $10^{-3}$ M, $10^{-2}$ M, or $10^{-1}$ M.

An agent is specific for a predetermined target if it is capable of binding to said predetermined target while it is not (substantially) capable of binding to other targets, i.e. has no significant affinity for other targets and does not significantly bind to other targets in standard assays. Preferably, an agent is specific for a predetermined target if the affinity for and the binding to such other targets does not significantly exceed the affinity for or binding to proteins which are unrelated to a predetermined target such as bovine serum albumin (BSA), casein or human serum albumin (HSA). Preferably, an agent is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an agent to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an agent to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, IC50, are preferably made with standardized solutions of antibody and antigen, and a standardized buffer.

The invention may involve introduction, i.e. transfection, of nucleic acids encoding antigen receptors into cells such as T cells in vitro or in vivo.

For purposes of the present invention, the term "transfection" includes the introduction of a nucleic acid into a cell or the uptake of a nucleic acid by a cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

According to the present invention, any technique useful for introducing, i.e. transferring or transfecting, nucleic acids into cells may be used. Preferably, nucleic acid such as RNA is transfected into cells by standard techniques. Such techniques include electroporation, lipofection and microinjection. In one particularly preferred embodiment of the present invention, RNA is introduced into cells by electroporation. Electroporation or electropermeabilization relates to a significant increase in the electrical conductivity and permeability of the cell plasma membrane caused by an externally applied electrical field. It is usually used in molecular biology as a way of introducing some substance into a cell. According to the invention it is preferred that introduction of nucleic acid encoding a protein or peptide into cells results in expression of said protein or peptide.

A variety of methods may be used to introduce antigen receptor constructs into T cells including non-viral-based DNA transfection, transposon-based systems and viral-based systems. Non-viral-based DNA transfection has low risk of insertional mutagenesis. Transposon-based systems can integrate transgenes more efficiently than plasmids that do not contain an integrating element. Viral-based systems include the use of γ-retroviruses and lentiviral vectors. γ-Retroviruses are relatively easy to produce, efficiently and permanently transduce T cells, and have preliminarily proven safe from an integration standpoint in primary human T cells. Lentiviral vectors also efficiently and permanently transduce T cells but are more expensive to manufacture. They are also potentially safer than retrovirus based systems.

For transfection of cells in vivo a pharmaceutical composition comprising nucleic acid encoding the antigen receptor may be used. A delivery vehicle that targets the nucleic acid to a specific cell such as a T cell may be administered to a patient, resulting in transfection that occurs in vivo.

According to the invention it is preferred to administer the nucleic acid encoding an antigen receptor in naked form or in a carrier. The carriers such as lipid carriers contemplated for use in the present invention include any substances or vehicles with which nucleic acid such as RNA can be associated, e.g. by forming complexes with the nucleic acid or forming vesicles in which the nucleic acid is enclosed or encapsulated. This may result in increased stability of the nucleic acid compared to naked nucleic acid. In particular, stability of the nucleic acid in blood may be increased. For example, nanoparticulate RNA formulations with defined particle size, such as lipoplexes from RNA and liposomes, e.g. lipoplexes comprising DOTMA and DOPE or DOTMA and Cholesterol, can be used.

As used herein, the term "nanoparticle" refers to any particle having a diameter making the particle suitable for systemic, in particular parenteral, administration, of, in particular, nucleic acids, typically a diameter of less than 1000 nanometers (nm). In some embodiments, a nanoparticle has a diameter of less than 600 nm. In some embodiments, a nanoparticle has a diameter of less than 400 nm.

As used herein, the term "nanoparticulate formulation" or similar terms refer to any substance that contains at least one nanoparticle. In some embodiments, a nanoparticulate composition is a uniform collection of nanoparticles. In some embodiments, nanoparticulate compositions are dispersions or emulsions. In general, a dispersion or emulsion is formed when at least two immiscible materials are combined.

The term, "lipoplex" or "nucleic acid lipoplex", in particular "RNA lipoplex", refers to a complex of lipids and nucleic acids, in particular RNA. Lipoplexes are formed spontaneously when cationic liposomes, which often also include a neutral "helper" lipid, are mixed with nucleic acids.

Cationic lipids, cationic polymers and other substances with positive charges may form complexes with negatively charged nucleic acids. These cationic molecules can be used to complex nucleic acids, thereby forming e.g. so-called lipoplexes or polyplexes, respectively, and these complexes have been shown to deliver nucleic acids into cells.

Nanoparticulate nucleic acid preparations for use in the present invention can be obtained by various protocols and from various nucleic acid complexing compounds. Lipids, polymers, oligomers, or amphipiles are typical complexing agents. In one embodiment, the complexing compound comprises at least one agent selected from the group consisting protamine, polyethyleneimine, a poly-L-lysine, a poly-L-arginine or a histone.

According to the invention, protamine is useful as cationic carrier agent. The term "protamine" refers to any of various strongly basic proteins of relatively low molecular weight that are rich in arginine and are found associated especially with DNA in place of somatic histones in the sperm cells of various animals (as fish). In particular, the term "protamine" refers to proteins found in fish sperm that are strongly basic, are soluble in water, are not coagulated by heat, and yield chiefly arginine upon hydrolysis. In purified form, they are used in a long-acting formulation of insulin and to neutralize the anticoagulant effects of heparin.

According to the invention, the term "protamine" as used herein is meant to comprise any protamine amino acid sequence obtained or derived from native or biological sources including fragments thereof and multimeric forms of said amino acid sequence or fragment thereof. Furthermore, the term encompasses (synthesized) polypeptides which are artificial and specifically designed for specific purposes and cannot be isolated from native or biological sources.

The protamine used according to the present invention can be sulfated protamine or hydrochloride protamine. In a preferred embodiment, the protamine source used for the production of the nanoparticles described herein is protamine 5000 which contains protamine at more than 10 mg/ml (5000 heparin-neutralizing units per ml) in an isotonic salt solution.

Liposomes are microscopic lipidic vesicles often having one or more bilayers of a vesicle-forming lipid, such as a phospholipid, and are capable of encapsulating a drug. Different types of liposomes may be employed in the context of the present invention, including, without being limited thereto, multilamellar vesicles (MLV), small unilamellar vesicles (SUV), large unilamellar vesicles (LUV), sterically stabilized liposomes (SSL), multivesicular vesicles (MV), and large multivesicular vesicles (LMV) as well as other bilayered forms known in the art. The size and lamellarity of the liposome will depend on the manner of preparation and the selection of the type of vesicles to be used will depend on the preferred mode of administration. There are several other forms of supramolecular organization in which lipids may be present in an aqueous medium, comprising lamellar phases, hexagonal and inverse hexagonal phases, cubic phases, micelles, reverse micelles composed of monolayers. These phases may also be obtained in the combination with DNA or RNA, and the interaction with RNA and DNA may substantially affect the phase state. The described phases may be present in the nanoparticulate nucleic acid formulations of the present invention.

For formation of nucleic acid lipoplexes from nucleic acid and liposomes, any suitable method of forming liposomes can be used so long as it provides the envisaged nucleic acid lipoplexes. Liposomes may be formed using standard methods such as the reverse evaporation method (REV), the ethanol injection method, the dehydration-rehydration method (DRV), sonication or other suitable methods.

After liposome formation, the liposomes can be sized to obtain a population of liposomes having a substantially homogeneous size range.

Bilayer-forming lipids have typically two hydrocarbon chains, particularly acyl chains, and a head group, either polar or nonpolar. Bilayer-forming lipids are either composed of naturally-occurring lipids or of synthetic origin, including the phospholipids, such as phosphatidylcholine, phosphatidylethanolamine, phosphatide acid, phosphatidylinositol, and sphingomyelin, where the two hydrocarbon chains are typically between about 14-22 carbon atoms in length, and have varying degrees of unsaturation. Other suitable lipids for use in the composition of the present invention include glycolipids and sterols such as cholesterol and its various analogs which can also be used in the liposomes.

Cationic lipids typically have a lipophilic moiety, such as a sterol, an acyl or diacyl chain, and have an overall net positive charge. The head group of the lipid typically carries the positive charge. The cationic lipid preferably has a positive charge of 1 to 10 valences, more preferably a positive charge of 1 to 3 valences, and more preferably a positive charge of 1 valence. Examples of cationic lipids include, but are not limited to 1,2-di-O-octadecenyl-3-trimethylammonium propane (DOTMA); dimethyldioctadecylammonium (DDAB); 1,2-dioleoyl-3-trimethylammonium-propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-dimyristoyloxypropyl-1,3-dimethylhydroxyethyl ammonium (DMRIE), and 2,3-dioleoyloxy-N-[2(spermine carboxamide)ethyl]-N,N-dimethyl-1-propanamium trifluoroacetate (DOSPA). Preferred are DOTMA, DOTAP, DODAC, and DOSPA. Most preferred is DOTMA.

In addition, the nanoparticles described herein preferably further include a neutral lipid in view of structural stability and the like. The neutral lipid can be appropriately selected in view of the delivery efficiency of the nucleic acid-lipid complex. Examples of neutral lipids include, but are not limited to, 1,2-di-(9Z-octadecenoyl)-sn-glycero-3-phosphoethanolamine (DOPE), 1,2-dioleoyl-sn-glycero-3-phosphocholine (DOPC), diacylphosphatidyl choline, diacylphosphatidyl ethanol amine, ceramide, sphingoemyelin, cephalin, sterol, and cerebroside. Preferred is DOPE and/or DOPC. Most preferred is DOPE. In the case where a cationic liposome includes both a cationic lipid and a neutral lipid, the molar ratio of the cationic lipid to the neutral lipid can be appropriately determined in view of stability of the liposome and the like.

According to one embodiment, the nanoparticles described herein may comprise phospholipids. The phospholipids may be a glycerophospholipid. Examples of glycerophospholipid include, without being limited thereto, three types of lipids: (i) zwitterionic phospholipids, which include, for example, phosphatidylcholine (PC), egg yolk phosphatidylcholine, soybean-derived PC in natural, partially hydrogenated or fully hydrogenated form, dimyristoyl phosphatidylcholine (DMPC) sphingomyelin (SM); (ii) negatively charged phospholipids: which include, for example, phosphatidylserine (PS), phosphatidylinositol (PI), phosphatidic acid (PA), phosphatidylglycerol (PG) dipalmipoyl PG, dimyristoyl phosphatidylglycerol (DMPG); synthetic derivatives in which the conjugate renders a zwitterionic phospholipid negatively charged such is the case of methoxy-polyethylene, gly col-distearoyl phosphatidylethanolamine (mPEG-DSPE); and (iii) cationic phospholipids, which include, for example, phosphatidylcholine or sphingomyelin of which the phosphomonoester was O-methylated to form the cationic lipids.

Association of nucleic acid to the lipid carrier can occur, for example, by the nucleic acid filling interstitial spaces of the carrier, such that the carrier physically entraps the nucleic acid, or by covalent, ionic, or hydrogen bonding, or by means of adsorption by non-specific bonds. Whatever the mode of association, the nucleic acid must retain its therapeutic, i.e. encoding, properties.

According to the invention, the nucleic acid encoding an antigen receptor in one embodiment is RNA, preferably mRNA. The RNA is preferably obtained by in-vitro transcription.

The term "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA. According to the invention, a nucleic acid is preferably an isolated nucleic acid.

Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a (3-D-ribofuranosyl) group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). mRNA has a limited half-time in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In one embodiment of the present invention, RNA is self-replicating RNA, such as single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. In one embodiment, the self-replicating RNA is a viral gene expression vector. In one embodiment, the virus is Semliki forest virus. In one embodiment, the self-replicating RNA contains one or more transgenes at least one of said transgenes encoding the agents described herein. In one embodiment, if the RNA is viral RNA or derived from viral RNA, the transgenes may partially or completely replace viral sequences such as viral sequences encoding structural proteins. In one embodiment, the self-replicating RNA is in vitro transcribed RNA.

In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or synthetic ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the insertion of one or more, preferably two copies of a 3'-UTR derived from a globin gene, such as alpha2-globin, alpha1-globin, beta-globin, preferably beta-globin, more preferably human beta-globin.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. In addition, incorporation of two or more 3'-non translated regions (UTR) into the 3'-non translated region of an RNA molecule can result in an enhancement in translation efficiency. In one particular embodiment the 3'-UTR is derived from the human β-globin gene.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

Nucleic acids may, according to the invention, be present alone or in combination with other nucleic acids, which may be homologous or heterologous. In preferred embodiments, a nucleic acid is functionally linked to expression control sequences which may be homologous or heterologous with respect to said nucleic acid. The term "homologous" means that the nucleic acids are also functionally linked naturally and the term "heterologous" means that the nucleic acids are not functionally linked naturally.

A nucleic acid and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" or "expression control element" comprises according to the invention promoters, ribosome binding sites, enhancers and other control elements which regulate transcription of a gene or translation of an mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

According to the invention, the term "nucleic acid encoding" means that nucleic acid, if present in the appropriate environment, preferably within a cell, can be expressed to produce a protein or peptide it encodes.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptide", "peptide chain" and "protein" are synonyms and are used interchangeably herein.

As mentioned above, the amino acid sequences of the peptide chains and antigen receptors described herein can be modified so as to obtain variants of said amino acid sequences. Accordingly, the present invention includes variants of the peptide and protein sequences described herein and includes variants of naturally occurring amino acid sequences resulting in sequences which are functionally equivalent to said sequences, e.g. amino acid sequences exhibiting properties identical or similar to those of said sequences. Important properties are to retain binding of an antigen receptor to its target or transduction of the antigen binding signal to a cell such as a T cell. In one embodiment, a variant molecule or sequence is immunologically equivalent to its parental molecule or sequence.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present invention, the term "immunologically equivalent" is preferably used with respect to the immunological effects or properties of antigen receptors used for therapy.

It will be appreciated by those skilled in the art that in particular the sequences of the CDR sequences, hypervariable and variable regions can be modified without losing the ability to bind to a target. For example, CDR regions may be either identical or highly homologous to the regions of parental antibodies. By "highly homologous" it is contemplated that from 1 to 5, preferably from 1 to 4, such as 1 to 3 or 1 or 2 substitutions may be made in the CDRs.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the invention at least 40%, in particular at least 50%, at least 60%, at least 70%, at least 80%, at least 90% and preferably at least 95%, at least 98 or at least 99% identity of the amino acid residues.

According to the invention, a variant, fragment, part, portion or derivative of an amino acid sequence, peptide or protein preferably has a functional property of the amino acid sequence, peptide or protein, respectively, from which it has been derived, i.e. it is functionally equivalent. In one embodiment, a variant, fragment, part, portion or derivative of an amino acid sequence, peptide or protein is functionally equivalent such as immunologically equivalent to the amino acid sequence, peptide or protein, respectively, from which it has been derived. In one embodiment, the functional property is the property to bind to antigen or transduce the binding signal within a cell.

The term "derived" means according to the invention that a particular entity, in particular a particular sequence, is present in the object from which it is derived, in particular an organism or molecule. In the case of amino acid sequences, especially particular sequence regions, "derived" in particular means that the relevant amino acid sequence is derived from an amino acid sequence in which it is present.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid and transferred to a recipient can express the nucleic acid in the recipient. The term "cell" includes bacterial cells; other useful cells are yeast cells, fungal cells or mammalian cells. Suitable bacterial cells include cells from gram-negative bacterial strains such as strains of *Escherichia coli*, *Proteus*, and *Pseudomonas*, and gram-positive bacterial strains such as strains of *Bacillus, Streptomyces, Staphylococcus*, and *Lactococcus*. Suitable fungal cell include cells from species of *Trichoderma, Neurospora*, and *Aspergillus*. Suitable yeast cells include cells from species of *Saccharomyces* (Tor example *Saccharomyces cerevisiae*), *Schizosaccharomyces* (for example Schizo *saccharomyces pombe*), *Pichia* (for example *Pichia pastoris* and *Pichia* methanolicd), and *Hansenula*. Suitable mammalian cells include for example CHO cells, BHK cells, HeLa cells, COS cells, 293 HEK and the like. However, amphibian cells, insect cells, plant cells, and any other cells used in the art for the expression of heterologous proteins can be used as well. Mammalian cells are particularly preferred for adoptive transfer, such as cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. Particularly preferred cells for use according to the invention are immunoreactive or immune effector cells, in particular T cells.

A cell which comprises a nucleic acid molecule preferably express the peptide or protein encoded by the nucleic acid.

The term "clonal expansion" or "expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes. The term "priming" refers to a process wherein a T cell has its first contact with its specific antigen and causes differentiation into effector T cells.

The molecules such as nucleic acids, peptide chains or antigen receptors, or cells described herein may be recombinant and/or isolated.

The term "isolated" as used herein, is intended to refer to an entity which is substantially free of other molecules such as other cellular material. The term "isolated" preferably means that the isolated entity has been separated from its natural environment. An isolated entity may be in an essentially purified state. The term "essentially purified" preferably means that the entity is essentially free of other substances with which it is associated in nature or in vivo.

The term "recombinant" in the context of the present invention means "made through genetic engineering". Preferably, a "recombinant object" such as a recombinant cell in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

"Reduce" or "inhibit" as used herein means the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%.

Since an antigen receptor of the present invention can be engineered to target virtually any antigen, including disease-specific antigens, an antigen receptor of the present invention has a broad therapeutic use. Accordingly, the present invention is directed to the use of an antigen receptor of the invention, its peptide chains, nucleic acids encoding same, and other related molecules in therapeutic and prophylactic methods. One such use is in the production of antigen-specific immune cells, which can be administered to a patient for preventing or treating a disease, which disease is characterized by expression of one or more antigens that can be bound by an antigen receptor of the invention expressed in the immune cells. Preferably, the disease is cancer. Further, an antigen receptor of the invention and related molecules also can be used for the selective eradication of cells expressing a predetermined antigen, as well as for immunization or vaccination against a disease wherein a predetermined antigen is expressed, which antigen can be bound by at least one antigen binding site of an antigen receptor of the invention.

In one embodiment, a method of treating or preventing a disease comprises administering to a patient an effective amount of a nucleic acid encoding an antigen receptor of the invention, in which at least one antigen binding site of the antigen receptor is able to bind an antigen that is associated with the disease (e.g., a viral or tumor antigen) to be treated or prevented. In another embodiment, a method of treating or preventing a disease comprises administering to a patient an effective amount of a recombinant immune effector cell or an expanded population of said immune effector cells, which immune effector cell or population of cells recombinantly express an antigen receptor of the invention, in which at least one antigen binding site of the antigen receptor is able to bind an antigen that is associated with the disease to be treated or prevented. In preferred embodiments, the disease is cancer and the antigen is a tumor associated antigen.

In another embodiment, the present invention provides for a method of immunizing or vaccinating against a disease associated with a specific antigen or against a disease-causing organism expressing a specific antigen, which method comprises administering to a patient an effective amount of a nucleic acid encoding an antigen receptor of the invention, in which at least one antigen binding site of the antigen receptor is able to bind the specific antigen. In another embodiment, the present invention provides for a method of immunizing or vaccinating against a disease associated with a specific antigen or against a disease-causing organism expressing a specific antigen, which method comprises administering to a patient an effective amount of a recombinant immune effector cell or an expanded population of said immune effector cells, which immune effector cell or population of cells recombinantly express an antigen receptor of the invention, in which at least one antigen binding site of the antigen receptor is able to bind to the specific antigen.

In certain embodiments, the population of immune effector cells can be a clonally expanded population. The recombinant immune effector cells or populations thereof provide for therapeutic or prophylactic immune effector function in an antigen-specific manner. Preferably, an antigen receptor of the invention is expressed on the cell surface of the immune effector cell.

The cells used in connection with the therapeutic and prophylactic methods of the present invention are preferably immune effector cells and the immune effector cells are preferably T cells. In particular, the cells used herein are cytotoxic lymphocytes, preferably selected from cytotoxic T cells, natural killer (NK) cells, and lymphokine-activated killer (LAK) cells. Upon activation/stimulation, each of these cytotoxic lymphocytes triggers the destruction of target cells. For example, cytotoxic T cells trigger the destruction of target cells by either or both of the following means. First, upon activation, the T cells release cytotoxins such as perforin, granzymes, and granulysin. Perforin and granulysin create pores in the target cell, and granzymes enter the cell and trigger a caspase cascade in the cytoplasm that induces apoptosis (programmed cell death) of the cell. Second, apoptosis can be induced via Fas-Fas ligand interaction between the T cells and target tumor cells. The T cells and other cytotoxic lymphocytes will preferably be autologous cells, although heterologous cells or allogenic cells can be used.

Accordingly, the agents, compositions and methods described herein can be used to treat a subject with a disease, e.g., a disease characterized by the presence of diseased cells expressing an antigen. Particularly preferred diseases are cancer diseases.

The agents, compositions and methods described herein may also be used for immunization or vaccination to prevent a disease described herein.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes infectious diseases and cancer diseases, in particular those forms of cancer described herein. Any reference herein to cancer or particular forms of cancer also includes cancer metastasis thereof.

A disease to be treated according to the invention is preferably a disease involving an antigen. "Disease involving an antigen", "disease associated with expression or elevated expression of an antigen" or similar expressions means according to the invention that the antigen is expressed in cells of a diseased tissue or organ. Expression in cells of a diseased tissue or organ may be increased compared to the state in a healthy tissue or organ. In one embodiment, expression is only found in a diseased tissue, while expression in a healthy tissue is not found, e.g. expression is repressed. According to the invention, diseases involving an antigen include infectious diseases and cancer diseases, wherein the disease-associated antigen is preferably an antigen of the infectious agent and a tumor antigen, respectively. Preferably a disease involving an antigen preferably is a disease involving cells expressing an antigen, preferably on the cell surface.

The term "healthy" or "normal" refer to non-pathological conditions, and preferably means non-infected or non-cancerous.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases. Preferably, a "cancer disease" is characterized by cells expressing a tumor antigen and a cancer cell expresses a tumor antigen.

In one embodiment, a cancer disease is a malignant disease which is characterized by the properties of anaplasia, invasiveness, and metastasis. A malignant tumor may be contrasted with a non-cancerous benign tumor in that a malignancy is not self-limited in its growth, is capable of invading into adjacent tissues, and may be capable of spreading to distant tissues (metastasizing), while a benign tumor has none of those properties.

According to the invention, the term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

Lymphoma and leukemia are malignancies derived from hematopoietic (blood-forming) cells.

Blastic tumor or blastoma is a tumor (usually malignant) which resembles an immature or embryonic tissue. Many of these tumors are most common in children.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

Infectious diseases that can be treated or prevented by the present invention are caused by infectious agents including, but not limited to, viruses, bacteria, fungi, protozoa, helminths, and parasites.

Infectious viruses of both human and non-human vertebrates, include retroviruses, RNA viruses and DNA viruses. Examples of virus that have been found in humans include but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hanta viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Retroviruses that are contemplated include both simple retroviruses and complex retroviruses. The complex retroviruses include the subgroups of lentiviruses, T cell leukemia viruses and the foamy viruses. Lentiviruses include HIV-1, but also include HIV-2, SIV, Visna virus, feline immunodeficiency virus (FIV), and equine infectious anemia virus (EIAV). The T cell leukemia viruses include HTLV-1, HTLV-II, simian T cell leukemia virus (STLV), and bovine leukemia virus (BLV). The foamy viruses include human foamy virus (HFV), simian foamy virus (SFV) and bovine foamy virus (BFV).

Bacterial infections or diseases that can be treated or prevented by the present invention are caused by bacteria including, but not limited to, bacteria that have an intracellular stage in its life cycle, such as mycobacteria (e.g., Mycobacteria tuberculosis, *M. bovis, M. avium, M. leprae*, or *M. africanum*), rickettsia, mycoplasma, chlamydia, and legionella. Other examples of bacterial infections contemplated include but are not limited to infections caused by Gram positive *bacillus* (e.g., *Listeria, Bacillus* such as *Bacillus anthracis, Erysipelothrix* species), Gram negative *bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio*, and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, Pneumococcus species, *Staphylococcus* species, *Neisseria* species. Specific examples of infectious bacteria include but are not limited to: *Helicobacter* pyloris, Borelia *burgdorferi, Legionella* pneumophilia, Mycobacteria tuberculosis, *M avium, M intracellulare*, M kansaii, *M gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus aecalis, Streptococcus bovis, Streptococcus pneumoniae, Haemophilus influenzae, Bacillus antracis, Corynebacterium diphtheriae, Erysipelothrix rhusiopathiae, Clostridium perfringens, Clostridium tetani, Enterobacter aerogenes, Klebsiella pneunmoniae, Pasteurella multocida, Fusobacterium nucleatuin, Streptobacillus moniliformis, Treponema pallidium, Treponema* pertenue, Leptospira, *Rickettsia*, and Actinoyyces israelli.

Fungal diseases that can be treated or prevented by the present invention include but are not limited to aspergilliosis, crytococcosis, sporotrichosis, coccidioidomycosis, paracoccidioidomycosis, histoplasmosis, blastomycosis, zygomycosis, and candidiasis.

Parasitic diseases that can be treated or prevented by the present invention include, but are not limited to, amebiasis, malaria, *leishmania*, coccidia, giardiasis, cryptosporidiosis, toxoplasmosis, and trypanosomiasis. Also encompassed are infections by various worms, such as but not limited to ascariasis, ancylostomiasis, trichuriasis, strongyloidiasis, toxoccariasis, trichinosis, onchocerciasis, filaria, and dirofilariasis. Also encompassed are infections by various flukes, such as but not limited to schistosomiasis, paragonimiasis, and clonorchiasis.

The term "treatment" or "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to human beings, non-human primates or other mammals (e.g. mouse, rat, rabbit, dog, cat, cattle, swine, sheep, horse or primate) that can be afflicted with or are susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient". The term "patient" means according to the invention a subject for treatment, in particular a diseased subject.

By "being at risk" is meant a subject, i.e. a patient, that is identified as having a higher than normal chance of developing a disease, in particular cancer, compared to the general population. In addition, a subject who has had, or who currently has, a disease, in particular cancer is a subject who has an increased risk for developing a disease, as such a subject may continue to develop a disease. Subjects who currently have, or who have had, a cancer also have an increased risk for cancer metastases.

The term "immunotherapy" relates to a treatment involving a specific immune reaction or response.

In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for a tumor, as described above, would be a candidate for therapy to prevent a tumor.

A prophylactic administration of an immunotherapy, for example, a prophylactic administration of an agent or composition of the invention, preferably protects the recipient from the development of a disease. A therapeutic administration of an immunotherapy, for example, a therapeutic administration of an agent or composition of the invention, may lead to the inhibition of the progress/growth of the disease. This comprises the deceleration of the progress/growth of the disease, in particular a disruption of the progression of the disease, which preferably leads to elimination of the disease.

Immunotherapy may be performed using any of a variety of techniques, in which agents provided herein preferably function to remove antigen-expressing cells from a patient. Such removal may take place as a result of enhancing or inducing an immune response in a patient specific for antigen or a cell expressing antigen.

The term "immunization" or "vaccination" describes the process of treating a subject with the purpose of inducing an immune response for therapeutic or prophylactic reasons.

The term "in vivo" relates to the situation in a subject.

The antigen receptors, peptide chains, nucleic acids, recombinant cells, immune effector cells, preferably T cells, of the invention, as well as other compounds and agents described herein may be administered in the form of any suitable pharmaceutical composition.

The pharmaceutical compositions of the invention are preferably sterile and contain an effective amount of the agents described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectable formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by expression of an antigen.

For example, in one embodiment, agents described herein can be used to treat a patient with a cancer disease, e.g., a cancer disease such as described herein characterized by the presence of cancer cells expressing an antigen.

The pharmaceutical compositions and methods of treatment described according to the invention may also be used for immunization or vaccination to prevent a disease described herein.

The pharmaceutical composition of the invention may be administered together with supplementing immunity-enhancing substances such as one or more adjuvants and may comprise one or more immunity-enhancing substances to further increase its effectiveness, preferably to achieve a synergistic effect of immunostimulation. The term "adjuvant" relates to compounds which prolongs or enhances or accelerates an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances, as explained above, are to be considered. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, IFNα, IFNγ, GM-CSF, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, are also suitable for use as adjuvants in the pharmaceutical composition of the present invention.

The pharmaceutical composition can be administered locally or systemically, preferably systemically.

The term "systemic administration" refers to the administration of an agent such that the agent becomes widely distributed in the body of an individual in significant amounts and develops a desired effect. For example, the agent may develop its desired effect in the blood and/or reaches its desired site of action via the vascular system. Typical systemic routes of administration include administration by introducing the agent directly into the vascular system or oral, pulmonary, or intramuscular administration wherein the agent is adsorbed, enters the vascular system, and is carried to one or more desired site(s) of action via the blood.

According to the present invention, it is preferred that the systemic administration is by parenteral administration. The term "parenteral administration" refers to administration of an agent such that the agent does not pass the intestine. The term "parenteral administration" includes intravenous administration, subcutaneous administration, intradermal administration or intraarterial administration but is not limited thereto.

Administration may also be carried out, for example, orally, intraperitoneally or intramuscularly.

The agents and compositions provided herein may be used alone or in combination with conventional therapeutic regimens such as surgery, irradiation, chemotherapy and/or bone marrow transplantation (autologous, syngeneic, allogeneic or unrelated).

The present invention is described in detail by the figures and examples below, which are used only for illustration purposes and are not meant to be limiting. Owing to the description and the examples, further embodiments which are likewise included in the invention are accessible to the skilled worker.

EXAMPLES

The techniques and methods used herein are described herein or carried out in a manner known per se and as described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information unless specifically indicated.

Figure 1:
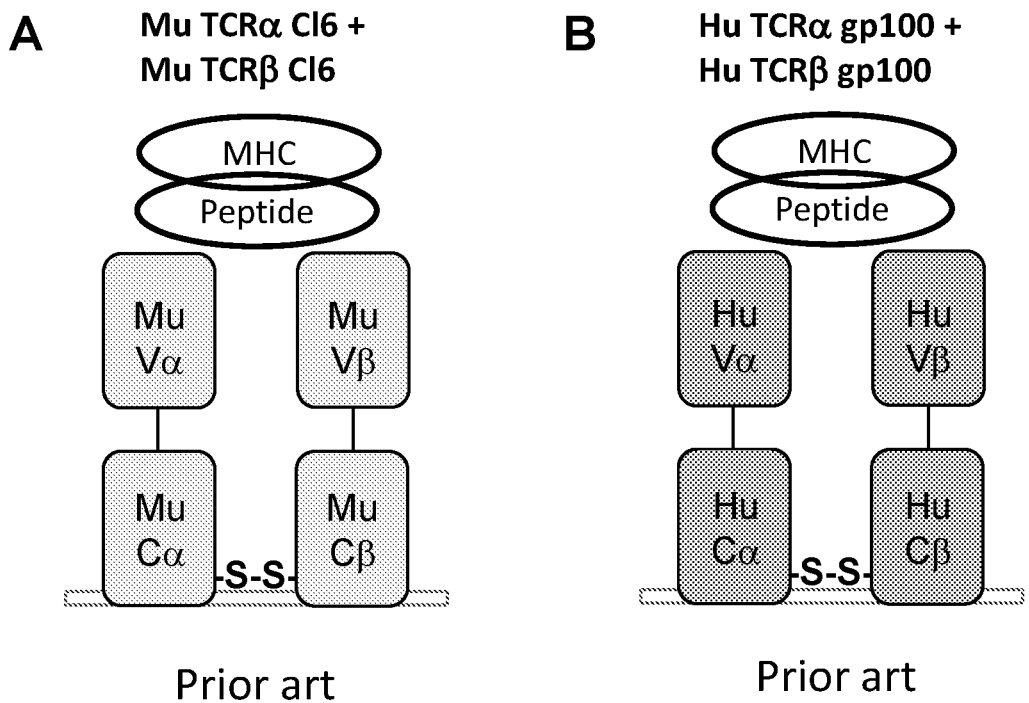
FIG. 1 comprises a schematic presentation of all T-cell receptor (TCR)- and chimeric antigen receptor (CAR)-constructs used in the experiments. A) and B) A TCR is composed of a heterodimeric class I membrane protein, each chain comprising an invariant C-domain and a variable V-domain, the latter specifically recognizing the processed peptide in an MHC-restricted manner. Sequence- and structure-homology of a murine (Mu, A) and a human (Hu, B) TCR is rather high. The murine TCR recognizes a human tumor antigen originating from the tight junction protein Claudin 6, while the human TCR recognizes a tumor antigen derived from the melanocyte differentiation antigen gp100. C) A monovalent single chain CAR comprises a single chain (sc) Fv-fragment hooked onto a murine Co-domain and an autonomous TCR Cα-domain, preceded by a signal peptide for export to the cell membrane. Optionally, it may be harnessed with an artificial disulfide bond between the TCR C-domains to improve cell surface expression and function of this CAR. The scFv-fragment in this and all following exemplary constructs are directed against Claudin 6. D) A classical scCAR C16 comprises a homodimer each lining up a scFv-fragment, an antibody hinge region, the CH2CH3-domains as spacer region, the cell membrane and intracellularly signaling domains of the costimulatory molecule CD28 and CD3ɛ, respectively. Homodimerisation leads to a bivalent recognition of the antigen, each chain binding a single antigen (i.e. intra-chain). E) A prototype combinatory CAR carries allele-related V-domains connected in series (i.e. VH-VH or VL-VL) and either hooked onto TCR Cα or Cβ, respectively. Recognition necessitates antigen binding across both chains in a combinatory (i.e. inter-chain) and bivalent fashion. F) A heterodimeric TCR-CAR C16 carrying scFv-fragments on either full length TCRa gp100 or TCR recognizes the cognate antigen in a bivalent, but non-combinatory way. G) In order to eliminate residual recognition of the cognate peptide gp100(280-288) by the TCR gp100 moiety of the non-combinatory TCR-CAR C16 (F), a 'silencing' (sil) S109Q (according IMGT nomenclature) point mutation is introduced into the CDR3 loop of TCRa (silCDR3α). H) A combinatory TCR-CAR C16 is generated by connecting the allele-related V-domains in series on either a full length TCRa gp100 chain or a full length TCR chain, respectively, as outlined in E). A full length TCR utilized as fusion partner here may provide a better physiologic T-cell signaling than a truncated TCR comprising merely the TCR C-domains instead (E). I) In order to eliminate residual recognition of the cognate peptide gp100(280-288) by the TCR gp100 moiety of the combinatory TCR-CAR C16 (H), a 'silencing' (sil) S109Q (according IMGT nomenclature) point mutation is introduced into the CDR3 loop of TCRa (silCDR3α) as in G).
Figure 1:
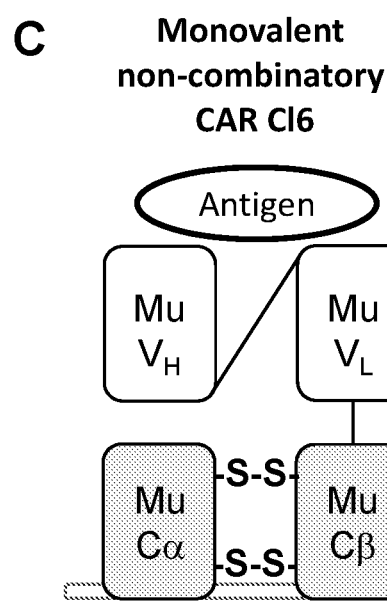
Figure 1:
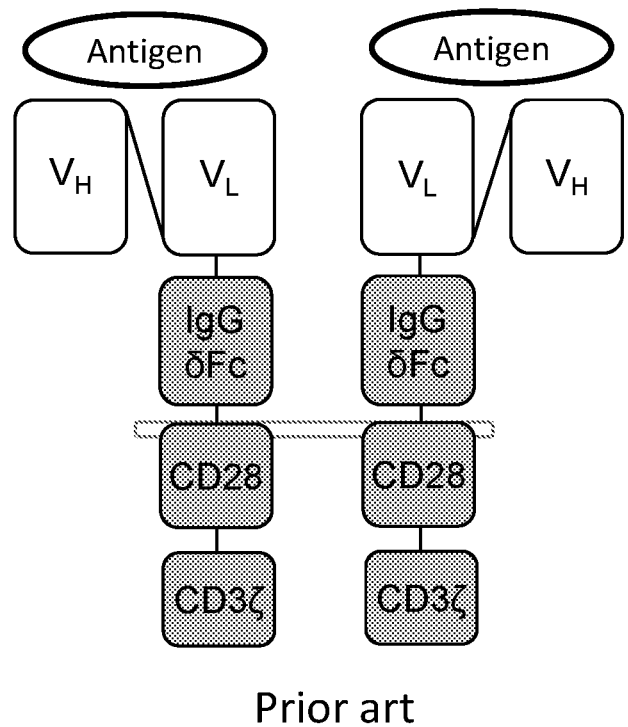
Figure 1:
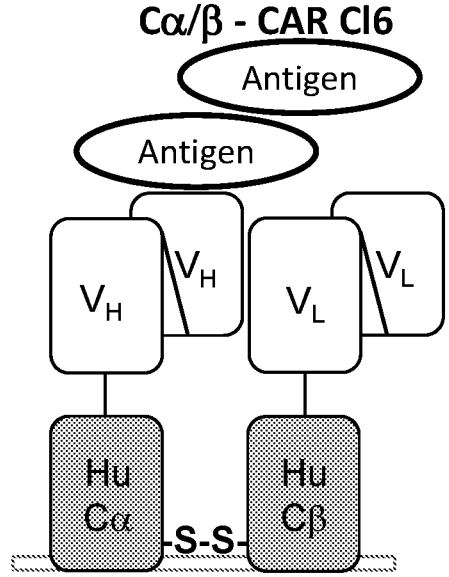
Figure 1:
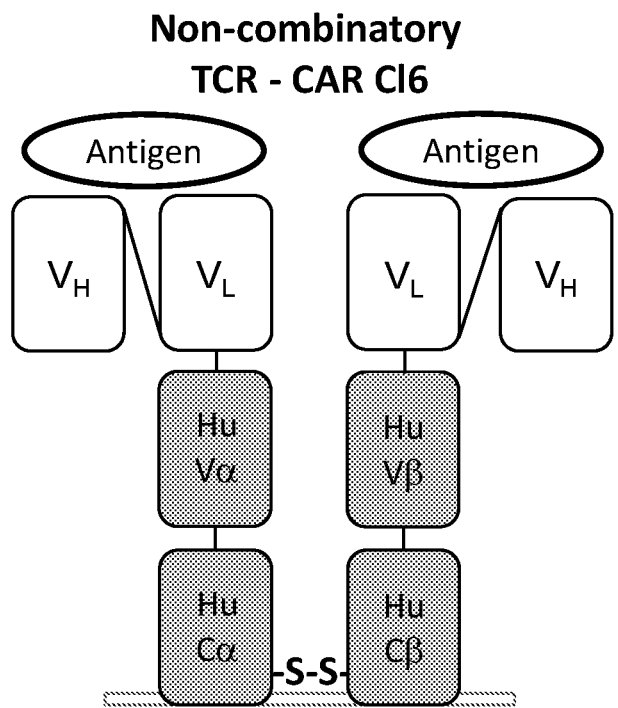
Figure 1:
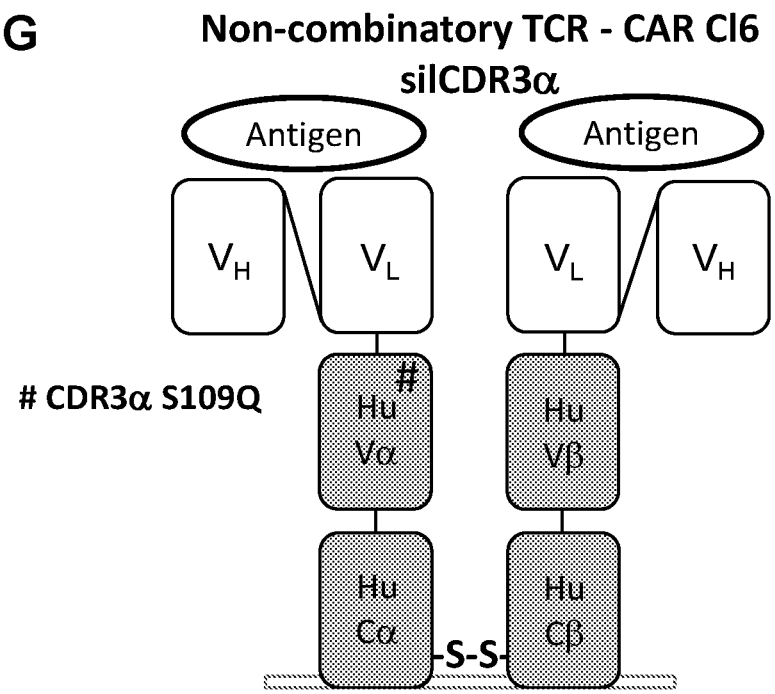
Figure 1:
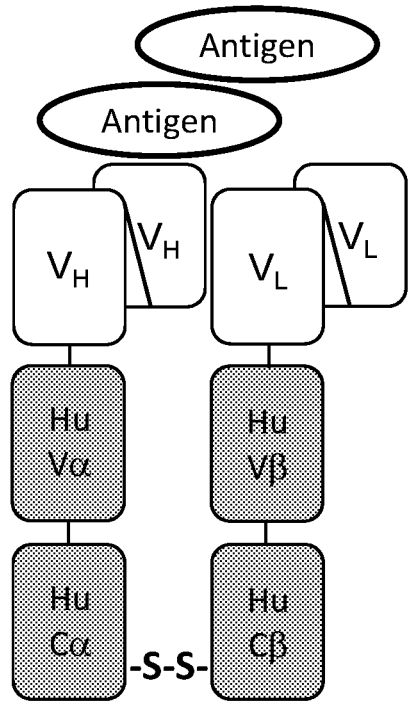
Figure 1:
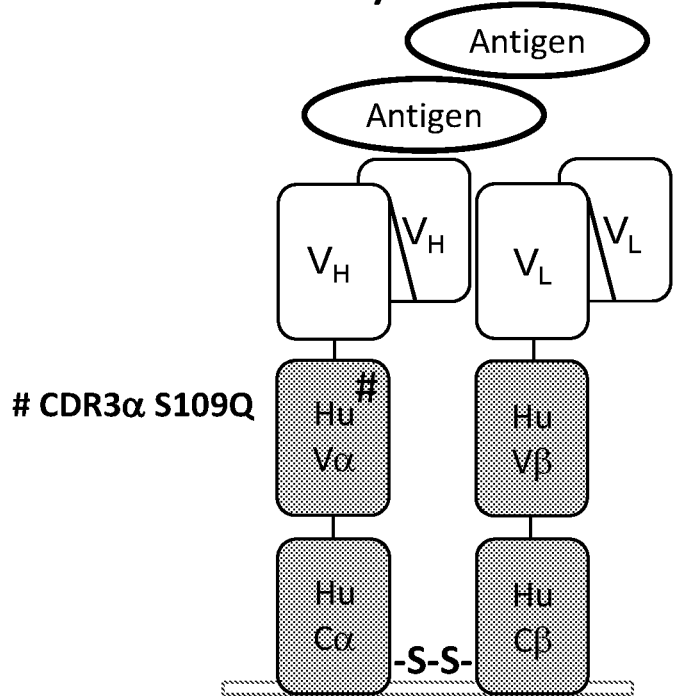
Figure 2A:
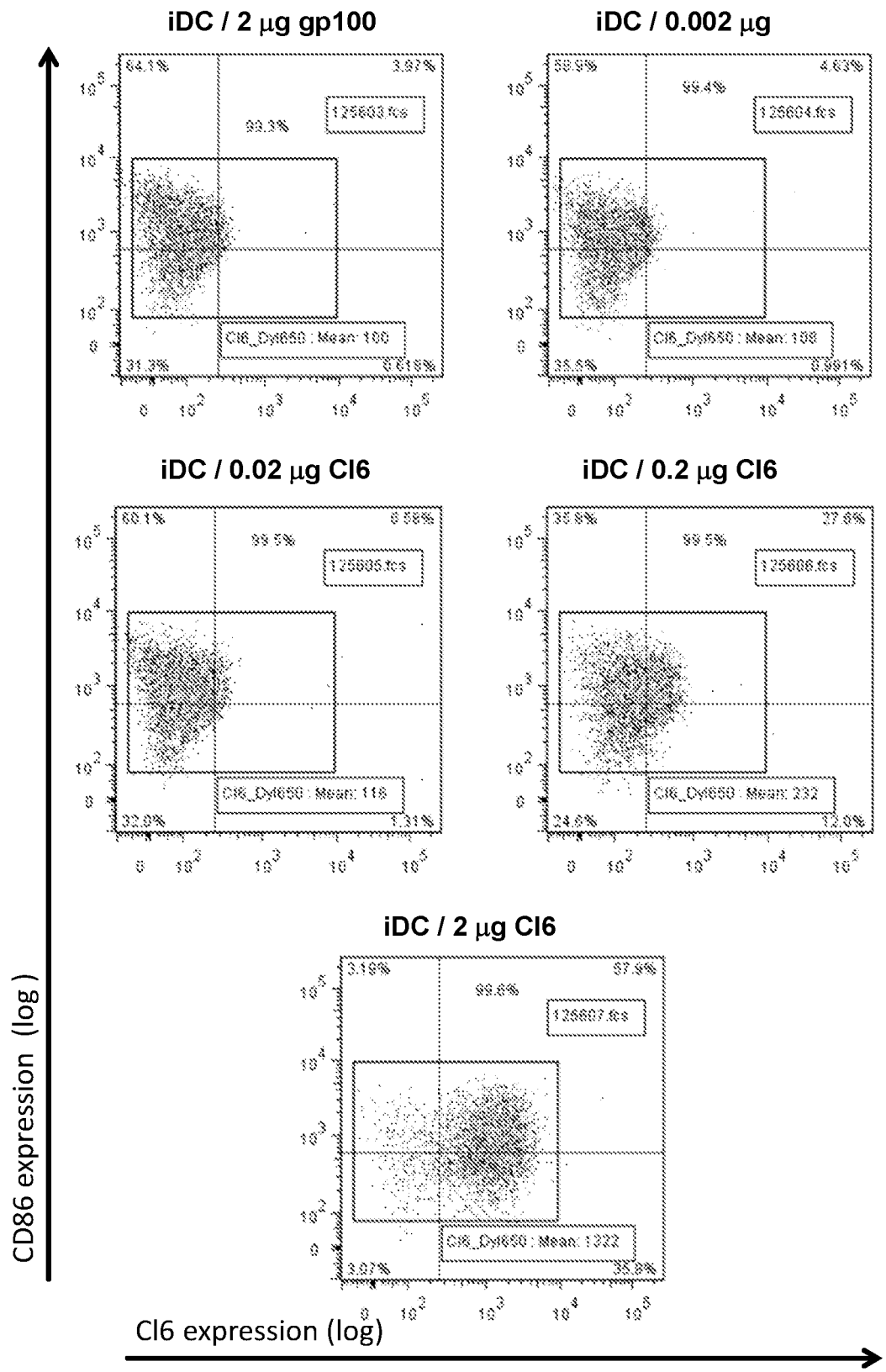
FIG. 2A/B shows expression of Claudin 6 on APCs and different CARs on human T-cells, respectively, prior to the setup of a coculture. A) Immature dendritic cells (iDCs) were electroporated with increasing amounts of the cognate full length antigen Claudin 6, or a single high dose of the irrelevant antigen gp100. Here, a dose-dependently bulk shift of C16-expression could be observed in flow cytometry, indicating that iDCs of this donor are highly permissive for cellular RNA uptake, protein translation and export to the cell surface. High CD86 expression indicates a strong differentiation of monocytes into favourably antigen-presenting iDCs. B) Preactivated CD8+ T-cells were electroporated with different CAR-encoding RNAs and assessed for CAR-expression in flow cytotmetry. All CARs except the monovalent and the classical scCAR, were moderately recovered in anti-idiotype staining. The monovalent CAR was expressed the least while the classical scCAR was found the best.

Example 1: Expression Analysis of Claudin 6 in iDCs and Antigen Receptors in T-Cells by Flow Cytometry RNA for the different constructs were prepared from in vitro transcription (ivt-RNA) of open reading frames (ORF) cloned into the RNA-vector pST1 carrying a T7 promoter at its 5'-leading sequence and an optimized polyA-tail at its 3'-tail. The expression of Claudin 6 in human immature dendritic cells was assessed one day after electroporation of RNA (2-0.002 µg, 300V, 12 ms, 1 pulse) into GM-CSF/IL-4 treated CD14+ monocytes from a buffy coat using a Claudin 6-specific antibody labeled with the fluorophore Dylight-650. The expression of various antigen receptor constructs in autologous human T-cells was assessed one day after electroporation of RNA (in total 10-30 µg for both chains, 495V, 9 ms, 1 pulse) into OKT3 (anti CD3ε murine monoclonal antibody)-preactivated CD8+ T cells using a C16 scFv idiotype-specific antibody labeled with the fluorophore Dylight-649. The detailed description for the preparation of human iDCs and T-cells is given in example 2. The CAR-constructs tested for expression were the (i) murine T cell receptor TCR C16; (ii) human TCR gp100; (iii) monovalent non-combinatory CAR C16; (iv) classical scCAR) (bivalent); (v) inter-combinatory CAR C16 fused to human TCR Cα/β-domains (bivalent); (vi) non-combinatory CAR C16 fused to full length TCR gp100(280-288) (bivalent); (vii) a corresponding non-combinatory CAR C16 additionally silenced in CDR3 of TCRα gp100 to eliminate peptide recognition (bivalent); (viii) inter-combinatory CAR C16 fused to full length TCR gp100(280-288) (bivalent) and (ix) a corresponding combinatory CAR C16 additionally silenced in CDR3 of TCRα gp100 to eliminate peptide recognition (bivalent). The different antigen receptor constructs are schematically illustrated in FIGS. 1A-I. Staining of the cells were routinely performed for 0.2×10$^6$ cells in flow cytometry buffer for 20 min at 4° C., washed and fixed with 1% paraformaldehyde-containing flow cytometry buffer. The data in FIG. 2A show the titrated expression of Claudin 6. Here, iDCs from this donor were highly permissive for C16 RNA and demonstrated a bulk shift of Claudin 6 expression with increasing amounts of electroporated RNA. CD86 expression indicated the successful differentiation of the monocytes into potent antigen presenting iDCs. FIG. 2B shows expression of the different CARs used in this experiment in human CD8-positively selected human T-cells. The classical scCAR C16 demonstrated the highest expression, presumably due to its endogenous CD3-independent expression on the T-cell surface. The combinatory CARs revealed a slightly better expression than the monovalent CAR, the latter which served as a 'weak control' due to its only monovalenty antigen binding mode of action.

Figure 3:
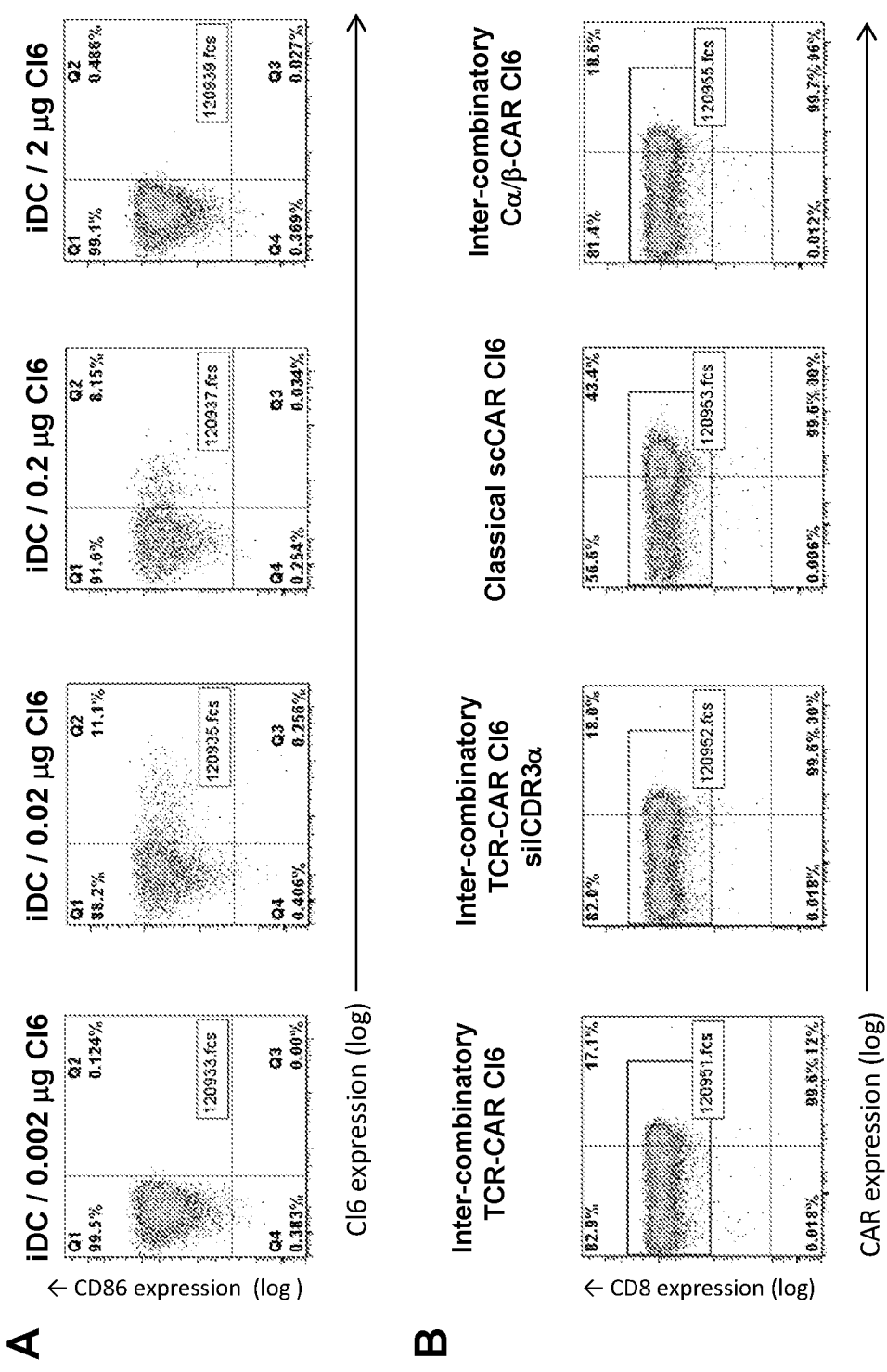
FIG. 3A/B shows expression of Claudin 6 on APCs and different CARs on human T-cells, respectively, prior to the setup of a coculture. A) Immature dendritic cells (iDCs) were electroporated with increasing amounts of the cognate full length antigen Claudin 6. Here, only a dose-dependently fractional shift of C16-expression could be observed in flow cytometry, indicating that iDCs of this donor are by far less permissive for cellular RNA uptake, protein translation and export to the cell surface. High CD86 expression indicates a strong differentiation of monocytes into favourably antigen-presenting iDCs. B) Preactivated CD8+ T-cells were electroporated with different CAR-encoding RNAs and assessed for CAR-expression in flow cytometry. All CARs except the monovalent and the classical scCAR, were only somewhat recovered in anti-idiotype staining, again indicating that cells of this donor are less permissive for RNA uptake and processing. However, the poorly antigen-presenting iDCs may represent a situation of minimally tumor antigen-positive APCs, as this may mimick the situation of early clonal tumor escape variants or minimal tumor antigen presentation.
FIG. 3C shows efficiency of CAR C16 reprogrammed human T-cells in recognizing Claudin 6 expressing iDCs after setup of APC/T-cell coculture in an IFNγ-ELISA. CAR-electroporated T-cells were cocultured overnight with C16-electroporated APCs as explained in 3A/B at an E:T-ratio of 10:1. Over the whole range of C16 titration all CARs elicited an optimum at lower C16 doses (0.2 ug). Due to minimal Claudin 6 expression at all as explained before, the combinatory CARs C16 demonstrated the best IFNγ-secretion in relation to the classical scCAR C16 for all doses, a trend that was even more pronounced at the lowest electroporated C16 dose. In conclusion, for tiny amounts of antigen the combinatory CARs were even better than the classical scCAR C16 with respect to IFNγ-secretion. The total amounts of secreted IFNγ dropped below 1.000 pg/ml for the whole titration range due to very low expression of antigen, and also the CARs.

The data in FIG. 3A show the titrated expression of Claudin 6 in an independent experiment. Here, iDCs from this donor were poorly permissive for C16 RNA and demonstrated an only fractional shift of Claudin 6 expression with increasing amounts of electroporated RNA. But CD86 expression indicated the successful differentiation of the monocytes into potent antigen presenting iDCs. FIG. 3B shows expression of the different CARs used in this experiment in human CD8– positively selected human T-cells. Since the human T-cells were derived from the same donor than the differentiated monocytes in an autologous setting, the T-cells turned out be also poorly permissive for electroporated RNA and yielded only weaker expression for the CARs than in the experiment shown in FIG. 2B. However, the classical scCAR C16 demonstrated again the highest expression for the same reason as outlined before. In line with the previous observations, the combinatory CARs revealed a slightly better expression than the monovalent CAR. Since the order of CAR-expression is preserved in comparison with the experiment outlined in FIG. 2A/B, this experiment is suited to study the potency of different CARs in case of only minute amounts of C16 expression on antigen presenting cells (APCs).

Example 2: Antigen-Titrated IFN-γ Secretion Assay

On day 1 of the experiment, fresh peripheral blood mononuclear cells ("PBMCs") were isolated from a buffy coat of one healthy donor. From ¼ of PBMCs, CD14+ cells were isolated using MACS sort. MACS flow through and residual PBMCs were then MACS sorted for CD8+ T cells. CD14+ cells were differentiated towards immature dendritic cells ("iDCs") by administration of IL-4 & GM-CSF (1000 U/ml) on day 1, 3, 6. CD8+ T cells were transferred on OKT3 coated 6 well plates. On day 3, T cells were transferred to new 6 well plates. On day 7, iDCs were electroporated with irrelevant and C16 ivt-RNA dose-dependently in the range of 2-0.002 μg RNA. OKT3 activated T cells were electroporated the same day with controls, or antigen receptor constructs as set forth in the individual figures and as described in Example 1. For quality assurance, C16 expression on iDCs and antigen receptor surface expression on T cells was analyzed with specific fluorescently-labeled antibodies as explained before on day 8. The electroporated T cells and antigen electroporated iDCs were subsequently co-cultured in a 96 well plate for 20 h at an E:T ratio of 3:1-10:1 in duplicates. Routinely, $2.5 \times 10^4$ iDCs were seeded and cocultured with $7.5 \times 10^4$-$2.5 \times 10^5$ CAR-electroporated T-cells in a volume of 200 μl T-cell medium. On day 9, different amounts of culture supernatants (10-50 μl) were taken and analyzed for the quantity of secreted IFNγ in a sandwich ELISA using the IFN-γ Ready Set Go! kit from eBioscience (#88-7316-88). Absorbance was detected using a Tecan Sunrise ELISA reader.

Figure 2C:
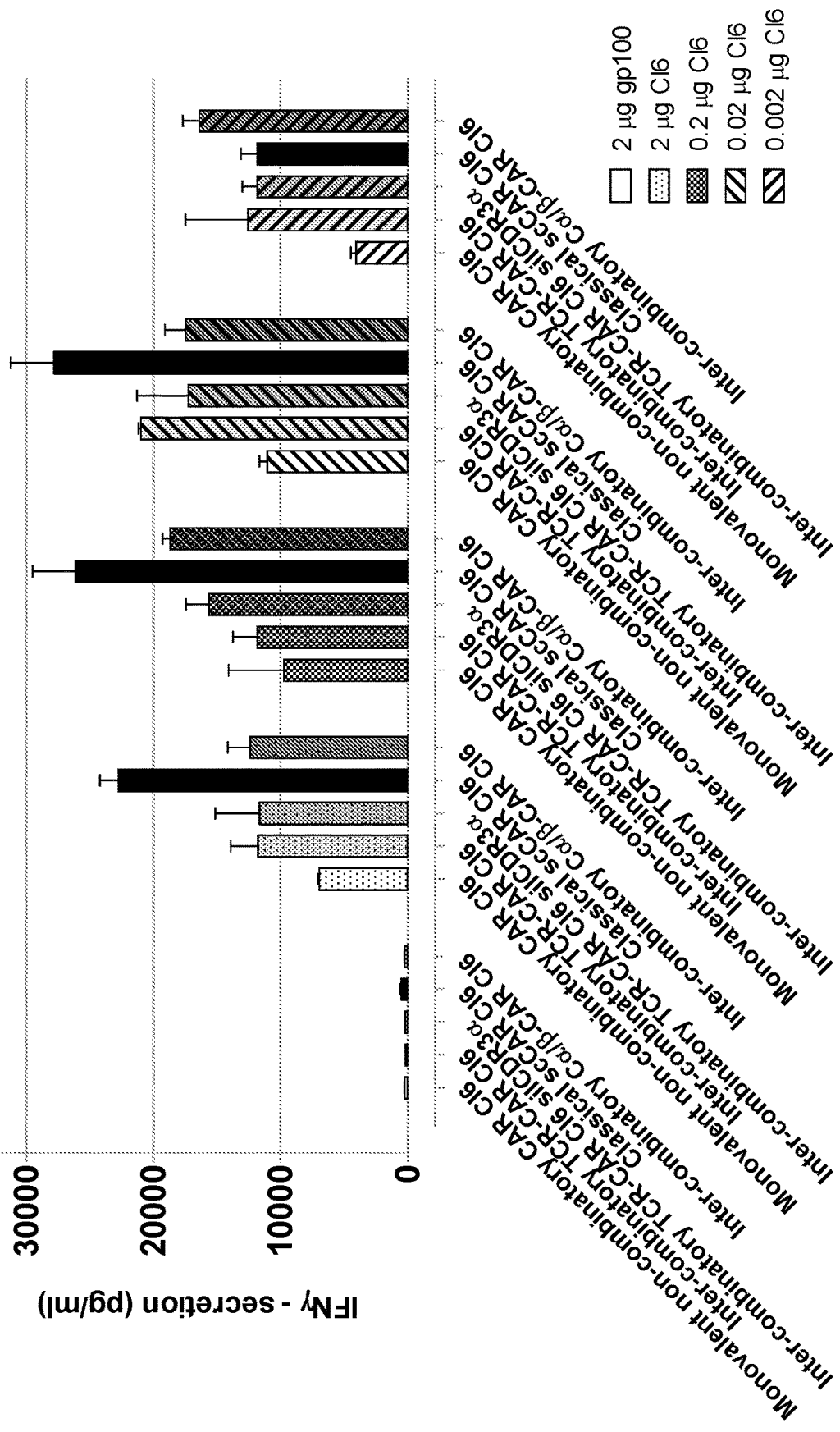
FIG. 2C shows efficiency of CAR C16 reprogrammed human T-cells in recognizing Claudin 6 expressing iDCs after setup of APC/T-cell coculture in an IFNγ-ELISA. CAR-electroporated T-cells were cocultured overnight with C16-electroporated APCs as explained in 2A/B at an E:T-ratio (effector to target cell ratio) of 10:1. Over the whole range of C16 titration all CARs elicited an optimum at lower C16 doses (0.02 ug). At high Claudin 6 expression, the classical scCAR C16 demonstrated the best IFNγ-secretion in relation to all other CARs while at the lowest C16 dose the combinatory CARs tended to be somewhat better than the classical scCAR. In conclusion, the combinatory CARs caught up with the classical CAR in their functional efficiencies from high to low antigen expression: They yielded very high amounts of IFNγ up to 20-30.000 pg/ml IFNγ for the combinatory CARs and the scCAR C16, respectively, and ended up with 12-15.000 pg/ml IFNγ for all constructs at the lowest dose of C16. At this dose, the inter-combinatory Ca/CP-CAR turned out to be the most efficient one.

FIG. 2C illustrates the amounts of secreted IFNγ for iDCs and T-cells of the same donor which were highly permissive for RNA electroporation and consequently, led to a bulk dose-dependent expression of C16 in iDCs and high expression of CARs in T-cells (FIG. 2A/B). All CAR T-cells exhibited their maximum in IFNγ-secretion at 0.02 μg of electroporated C16 RNA resulting in up to 30.000 pg/ml IFNγ for the classical scCAR and 20.000 pg/ml for the combinatory CARs either fused to TCR Cα/β or full-length TCR gp100. As estimated, the monovalent CAR-modified T-cells turned out to be the weakest effector cells. Intriguingly, at a high C16 electroporation level the combinatory CARs showed only approximately 50% of reactivity of that of the classical scCAR C16, which increased to 70% at the optimal dose of 0.02 μg electroporated C16. Importantly, at the lowest dose of C16 tested here, 0.002 μg RNA, the combinatory CARs were as efficient as the classical scCAR C16, or in case of the combinatory CAR fused to TCR Cα/β, even better. At this very low level of bulk presence of C16, the combinatory CARs were still able to secrete high amounts of IFNγ in the range of 10.000 pg/ml.

Figure 3C:
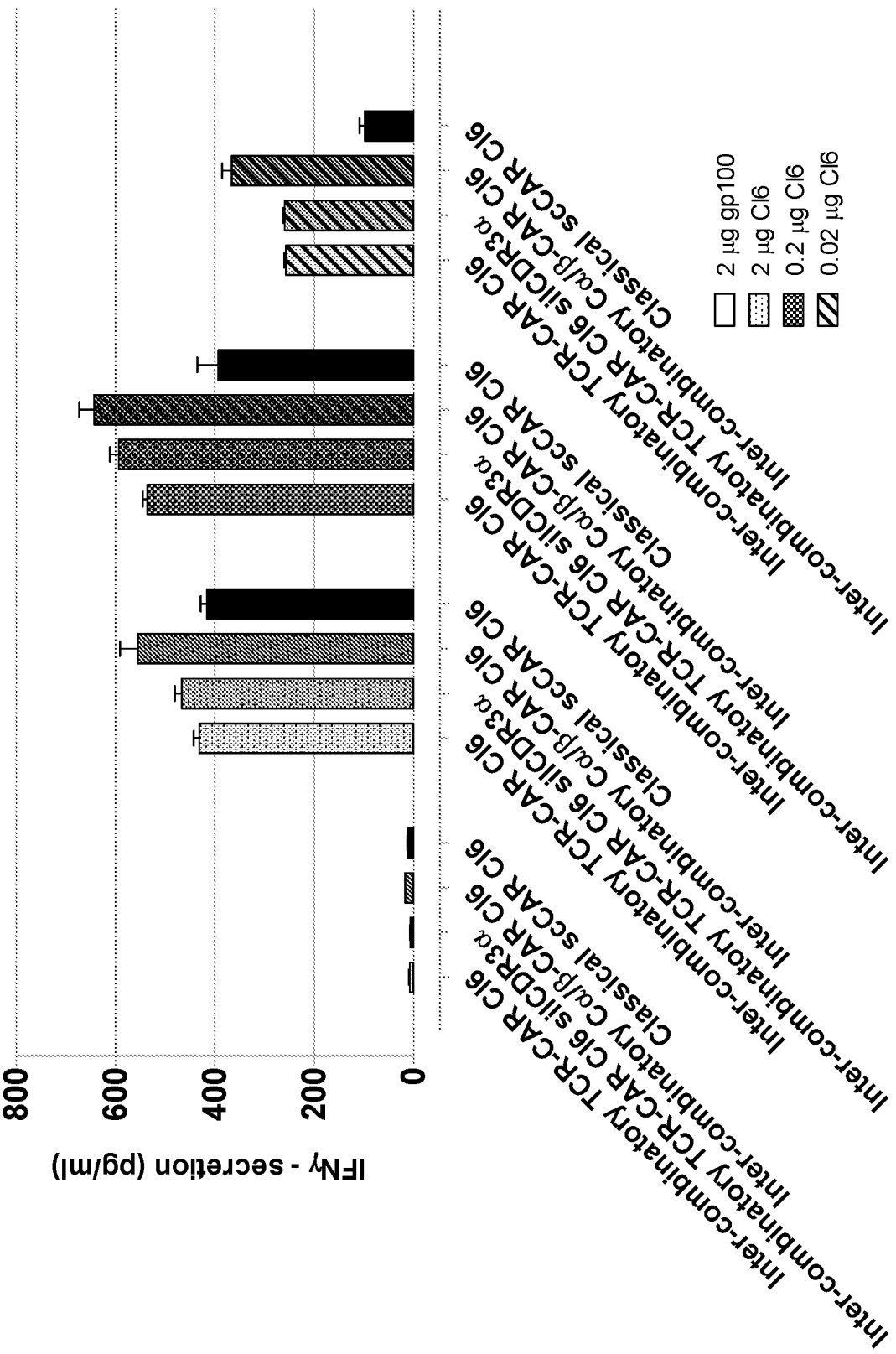

FIG. 3C exemplifies the amounts of secreted IFNγ for iDCs and T-cells of the same donor which were poorly permissive for RNA electroporation and consequently, led to only a fractional dose-dependent expression of C16 in iDCs and also lower expression of CARs in T-cells (FIG. 3A/B). This may constitute a situation of even less C16 to be found on iDCs than the situation for low C16 expression levels in highly permissive antigen-titrated iDCs (FIG. 3A/B versus 2A/B). Here, for all titrated tiny amounts of C16, the combinatory CARs proved to be more efficient in IFNγ-secretion than the classical scCAR. This trend even becomes more pronounced for decreasing amounts of C16 on the cell surface of iDCs. The amount of secreted IFNγ is low (<1000 pg/ml), but firstly may be improved by better CAR expression and secondly may become beneficial for patients in the clinic bearing very low antigen expressing (early) tumor escape variants or for tackling minimal residual disease.

Figure 4A:
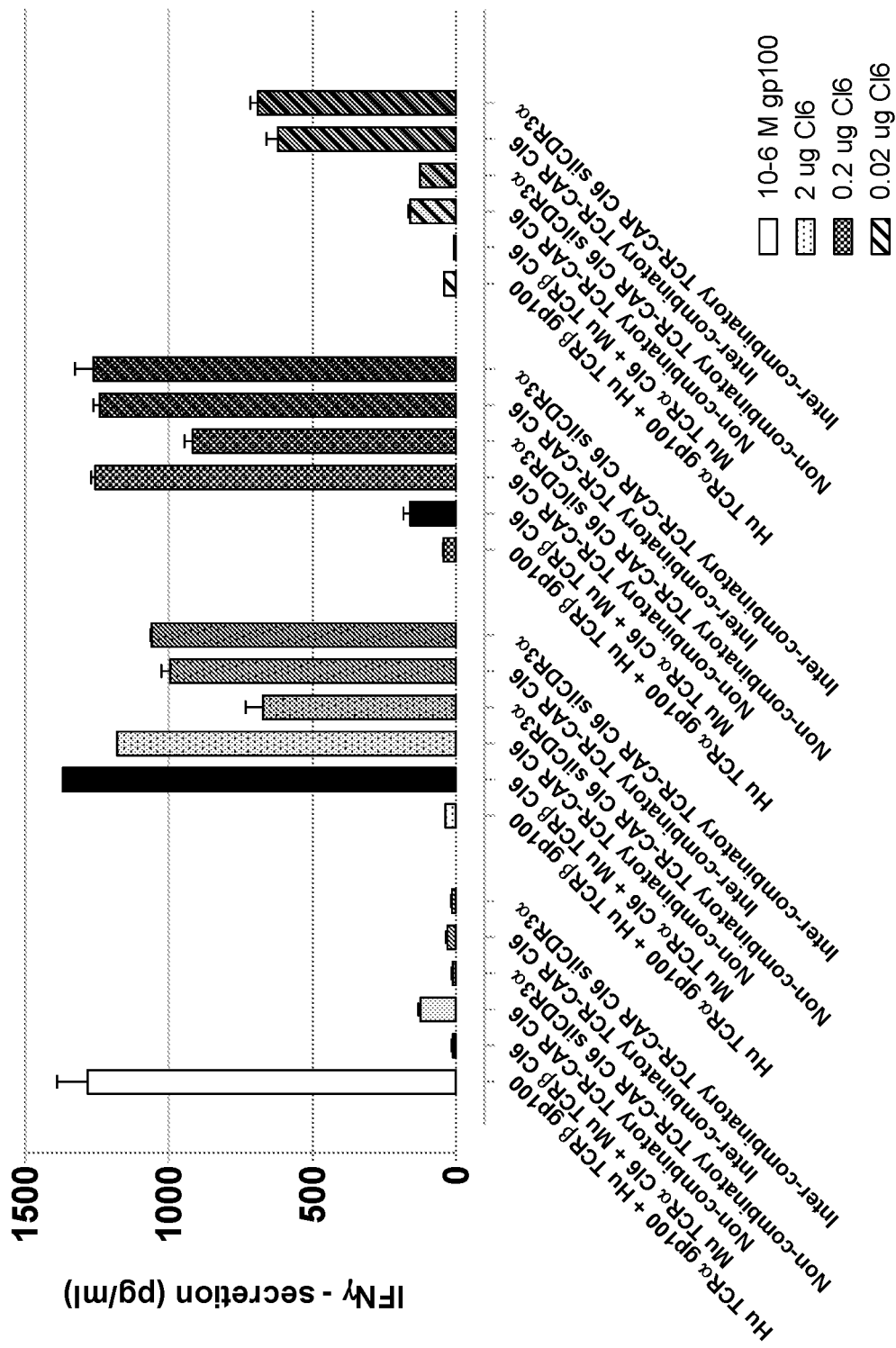
FIG. 4 depicts efficiency of TCR gp100-CAR C16 reprogrammed human T-cells in recognizing Claudin 6 expressing iDCs or gp100 peptide-loaded iDCs after setup of HLA-A2.1$^+$ APC/T-cell coculture in an IFNγ-ELISA. CAR-electroporated T-cells were cocultured overnight with C16-electroporated APCs or gp100(280-288) peptide-loaded iDCs at an E:T-ratio of 5:1. The ultimate goal of this experiment was to verify whether firstly (A) the bivalent combinatory TCR-CARs were more efficient in secreting IFNγ than the bivalent non-combinatory TCR-CARs and secondly (B), to what extent they still recognize the gp100 peptide of the TCR gp100 backbone used here. Residual antigen binding was tried to eliminate by a 'silencing' mutation S109Q in CDR3 of TCRα gp100. TCR C16 and TCR gp100 served as a positive control for cognate antigen recognition. A) The combinatory TCR-CARs, irrespective of being silenced in CDR3α or not, turned out to be more functional than the non-combinatory CARs particularly at the lowest dose of antigen. B) The non-silenced non-combinatory TCR-CAR C16 still recognized gp100 at $10^{-6}$ M peptide. Introduction of the mutation S109Q abolished IFNγ-secretion at all. For the combinatory TCR-CARs C16 no secretion of cytokine was observed at all irrespective of being functionally silenced or not. It is highly likely, that the inter-chain binding of serially connected VH-VH- and VL- VL-domains on either chain sterically prevents binding of the gp100 peptide, presented in a HLA-A2.1-restricted manner on APCs.

FIG. 4A compares the efficiency in IFNγ-secretion for (bivalent) non-combinatory versus combinatory TCR-CARs against the CAR-specific antigen C16. All combinatory CARs were more efficient in antigen recognition over a broad range of titrated antigen. For higher doses of antigen bivalent CARs were almost equal in effector function except the 'silenced' non-combinatory TCR-CAR. It is known that the S109Q point mutation in CDR3α impairs a little bit gp100(280-288)-antigen binding (Knies et al., Oncotarget 2016). The interchain-binding of V-domains and binding of antigen itself by the 'silenced' combinatory TCR-CAR apparently compensate for loss of function caused by this mutation. Importantly, at a low level of C16-expression (0.02 μg) the combinatory TCR-CARs, either functionally silenced or not, became superior to the non-combinatory TCR-CARs towards cytokine secretion.

Figure 4B:
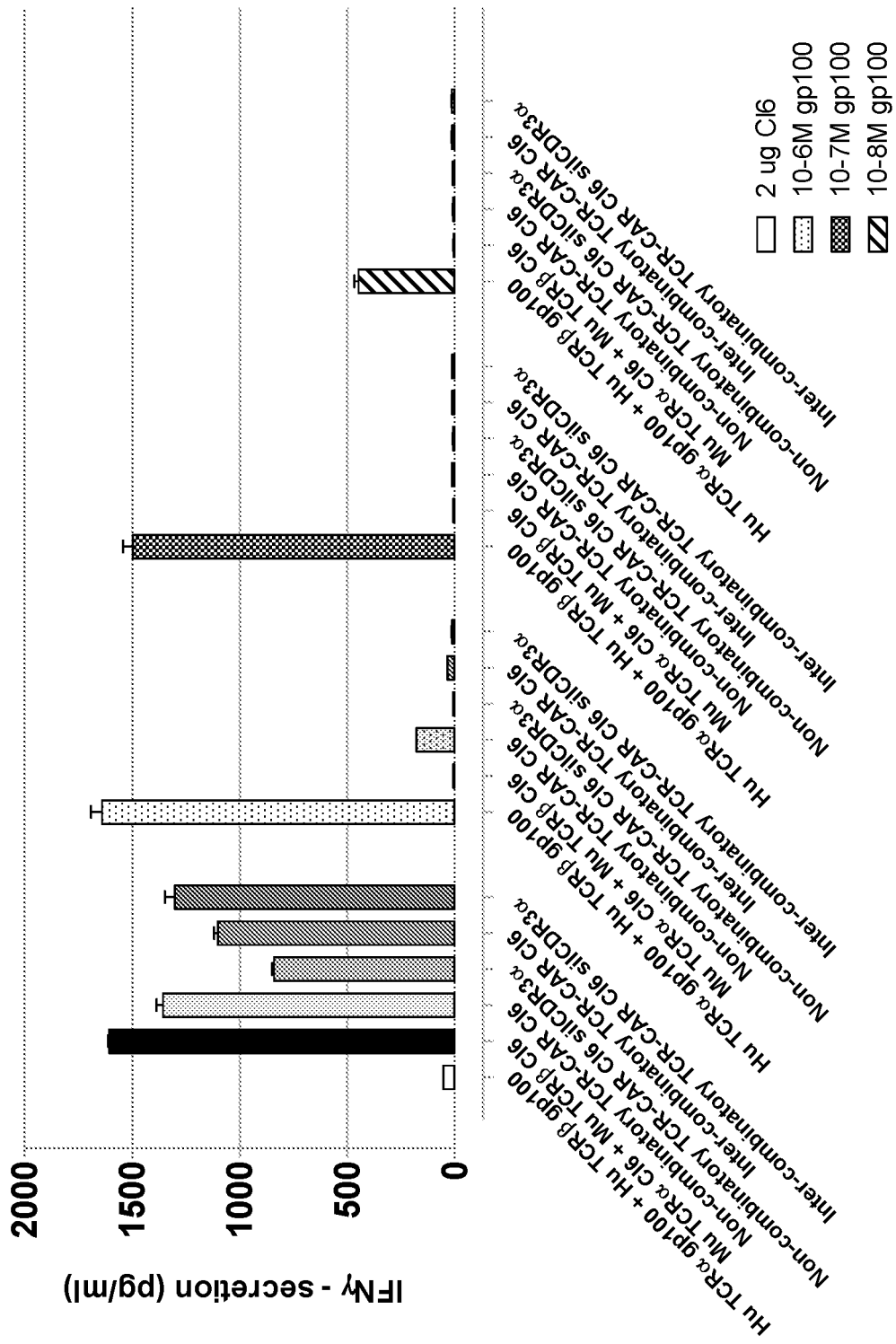

FIG. 4B illustrates the residual recognition of the gp100 (280-288) antigen in peptide-titrated IFNγ-secretion. Here, TCRαβ gp100 served as a positive control while TCRαβ C16 as a specificity control to estimate the background secretion of cytokine. The non-combinatory TCR-CAR is still able to recognize the A2-1-restricted antigen at high peptide load. Introduction of the silencing mutation S109Q abolished recognition at all. Importantly, the interchain combinatory arrangement of the V-domains connected in a tandem-order (VH-VH-, VL-VL-) seemed to prevent recognition of the cognate antigen by the TCR gp100 moiety entirely. Introduction of the silencing mutation may therefore serve just as a safeguard to warrant the functional unresponsiveness of the TCR moiety in these CARs and to focus on exploiting its backbone as a chain-pairing stabilizing scaffold and as a full length adaptor molecule for physiologic T-cell signaling.

Example 3: Antigen-Titrated Proliferation Assay Combined with Biomarker Phenotyping On day 1 of the experiment, fresh PBMCs were isolated from a buffy coat of a healthy donor. From ¼ of PBMCs, CD14+ cells were isolated using MACS sort, and residual PBMCs were frozen. CD14+ cells were differentiated to iDCs by administration of IL-4 & GM-CSF (1000 U/ml) on day 1, 3, 6. On day 7 iDCs were electroporated with irrelevant and C16 IVT-RNA dose-dependently in the range of 2-0.002 μg RNA. The frozen PBMCs were thawed on the same day and MACS sorted for CD8+ cells. Without any prior activation (OKT3), naïve T cells, approx. $7 \times 10^6$ cells, were subsequently electroporated with classical, monovalent and inter-combinatory TCR-CARs as indicated in FIG. 1.

For quality assurance, CAR-engineered T cells were analyzed by flow cytometry staining on day 8. T cells were subsequently labeled with the intracellularly fluorescent proliferation marker CFSE (0.8 μM) or CPD-450 (10 μM). The electroporated T cells and iDCs were subsequently co-cultured in a 96 well plate for 5 days at an E:T ratio of 10:1 (or 3:1 for biomarker phenotyping) in duplicates.

Routinely, 2.5×10⁴ iDCs were cocultured with 2.5×10⁵ CAR-electroporated T-cells in a volume of 200 μl T-cell medium in a 96-well plate. On day 5, cultured cells were stained in the 96 well plates with CD4 or CD8 antibodies labeled with APC-Cy7. Proliferation of T cells was detected via flow cytometry by the leftwards shift of the fluorophore-signal due to dilution in proliferating daughter cells. The frequencies of the non-proliferating parental population G0 and the daughter populations G1-G7 were assessed using the proliferation tool in the flow cytometry software package FlowJo v7.6.5. The frequencies for all daughter T-cells were calculated from the sum of all proliferating populations G1-G7. Background proliferation of T cells was assessed for cells cultured with iDCs electroporated with irrelevant full length gp100 or T-cells seeded without APCs. Proliferating cells were stained for CD8 to unequivocally identify them as T-cells. Alternatively, proliferating T-cells were stained with biomarkers such as CD27, CD28, PD-1, CD95, CD45RA, and CCR7 to quantify the differentiation status of the originally naïve non-proliferating T-cells in G0 and the evolving daughter populations G1-G7, respectively, after 5 or 6 days of coculture with APCs. Antibodies and corresponding isotype controls were titrated to estimate the optimal signal-to-noise ratio. The assay was quantified on a FACS-Canto II-HTS system (BD) in a 96 well-format.

Figure 5A:
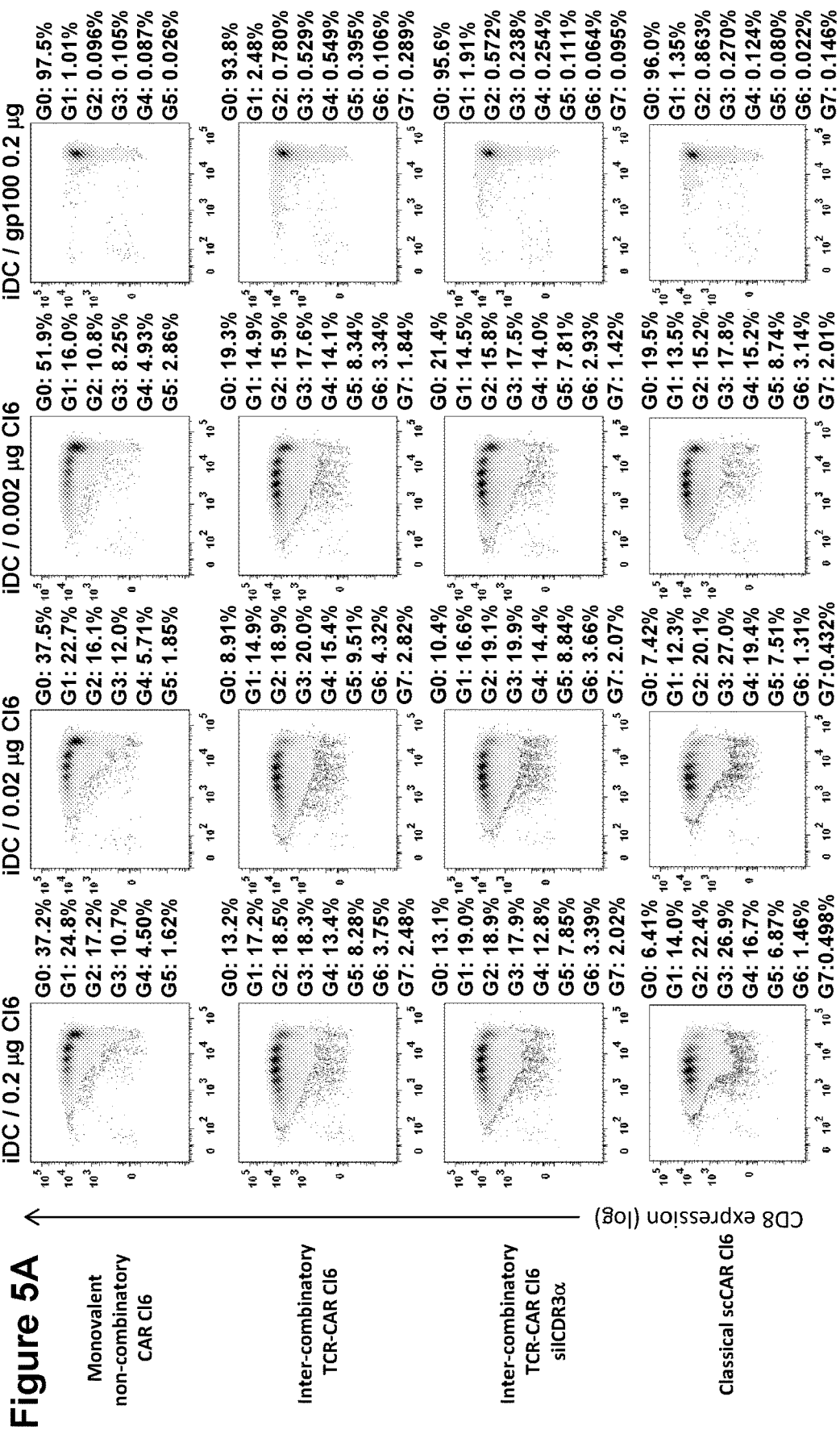
FIG. 5 illustrates proliferation capacity of different CARs C16 upon antigen encounter with C16-expressing iDCs after setup of an APC/T-cell coculture. CAR-electroporated T-cells were cocultured for 5 days with C16-electroporated and -titrated APCs at an E:T-ratio of 10:1. T-cells were priorly stained with Carboxyfluorescein succinimidyl ester (CFSE) to quantify the dilution of CFSE by cell divisions and so, the number and frequency of resulting daughter populations indicated on the right of each density plot in flow cytometry. A) Monovalently antigen-binding CARs exhibited the weakest proliferation while the combinatory TCR-CARs and classical CARs showed a very similar proliferation pattern. B) Bar chart for frequencies of T-cell populations shown in A). A high frequency of T-cells equipped with the monovalent CAR did not proliferate (40-60%) while the frequency of non-proliferating T-cells for combinatory TCR-CARs and classical CAR were approximately in the range of 10-20%. Proliferation of T-cells carrying the classical CAR C16 was the highest at high dose (0.2 µg C16) of antigen (90% versus 80% for combinatory TCR-CARs), while at the lowest dose (0.002 µg) the combinatory TCR-CARs were at least as potent as the classical CAR (almost 80%). Conclusively, the combinatory TCR-CARs again caught up with the classical CAR in their functional efficiencies, here in terms of T-cell proliferation, from high to very low doses of antigen. There is a trend towards being even more effective than the classical CAR.

FIG. 5A depicts the density plots of proliferating T-cells engineered with monovalent CAR C16 as a 'weak control', combinatory TCR-CARs without and with the silencing mutation S109Q in TCR CDR3α, and the classical scCAR C16 as reference CAR. Almost no unspecific proliferation could be observed against iDCs loaded with the irrelevant antigen gp100. Proliferation against APCs loaded with the cognate antigen resulted in up to 6 distinct daughter populations, whose frequencies could be easily discerned (listed rightwards of each plot). All CARs except the monovalent CAR C16 showed high proliferation rates even at low antigen densities. The maximal frequencies were in almost all cases in G3.

Figure 5B:
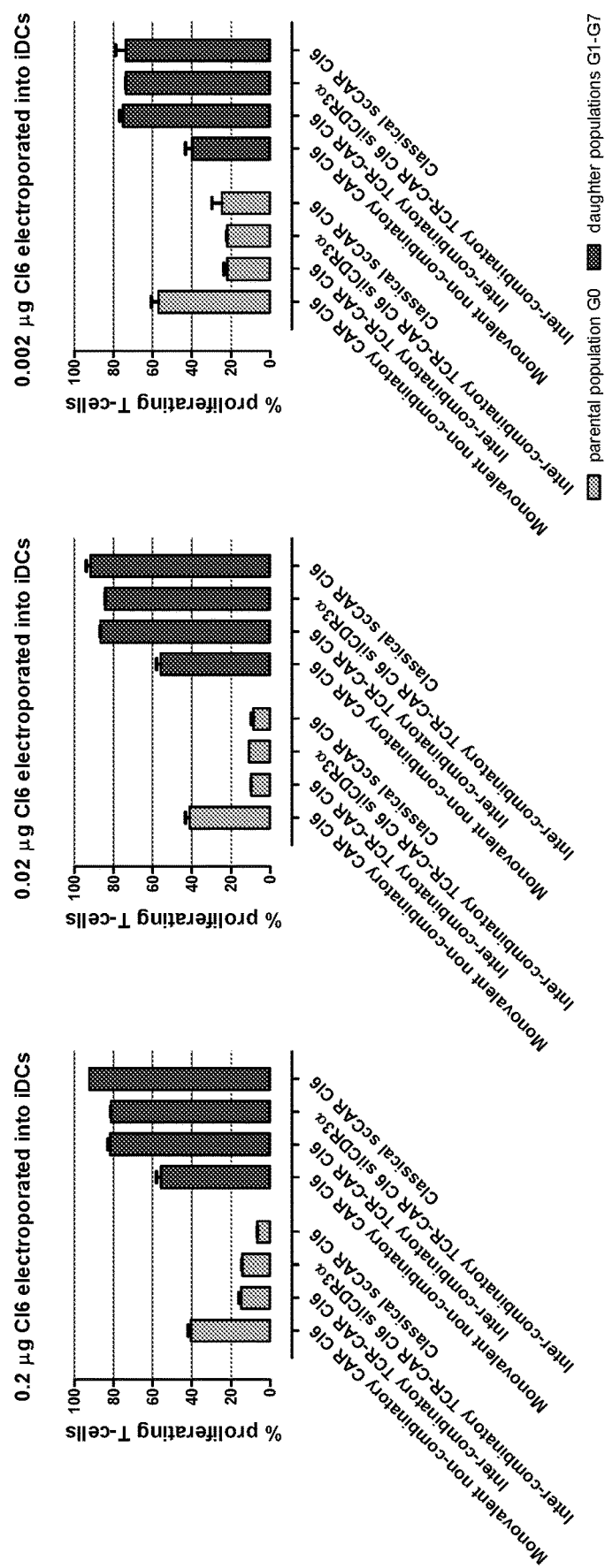

FIG. 5B summarizes the percentages of remaining parental T-cells G0 and proliferating T-cells G1-G7 in a bar chart. At high antigen load, the large bar for G0 (40%) and the smaller bar for G1-G7 (60%) in comparison to the other CARs clearly indicates the weak propensity of the monovalent CAR-engineered T-cells to proliferate. The classical scCAR-modified T-cells proved to be somewhat better (90%) than the combinatory CARs (80%) in line with results from IFNγ-secretion assays. Consequently, when decreasing the amount of antigen, the combinatory CAR-modified T-cells became at least as efficient as the classical scCAR (almost 80%). From this trend one may speculate that for even lower antigen densities the combinatory CARs may become even more superior to the classical scCAR in terms of proliferation potency.

Figure 6:
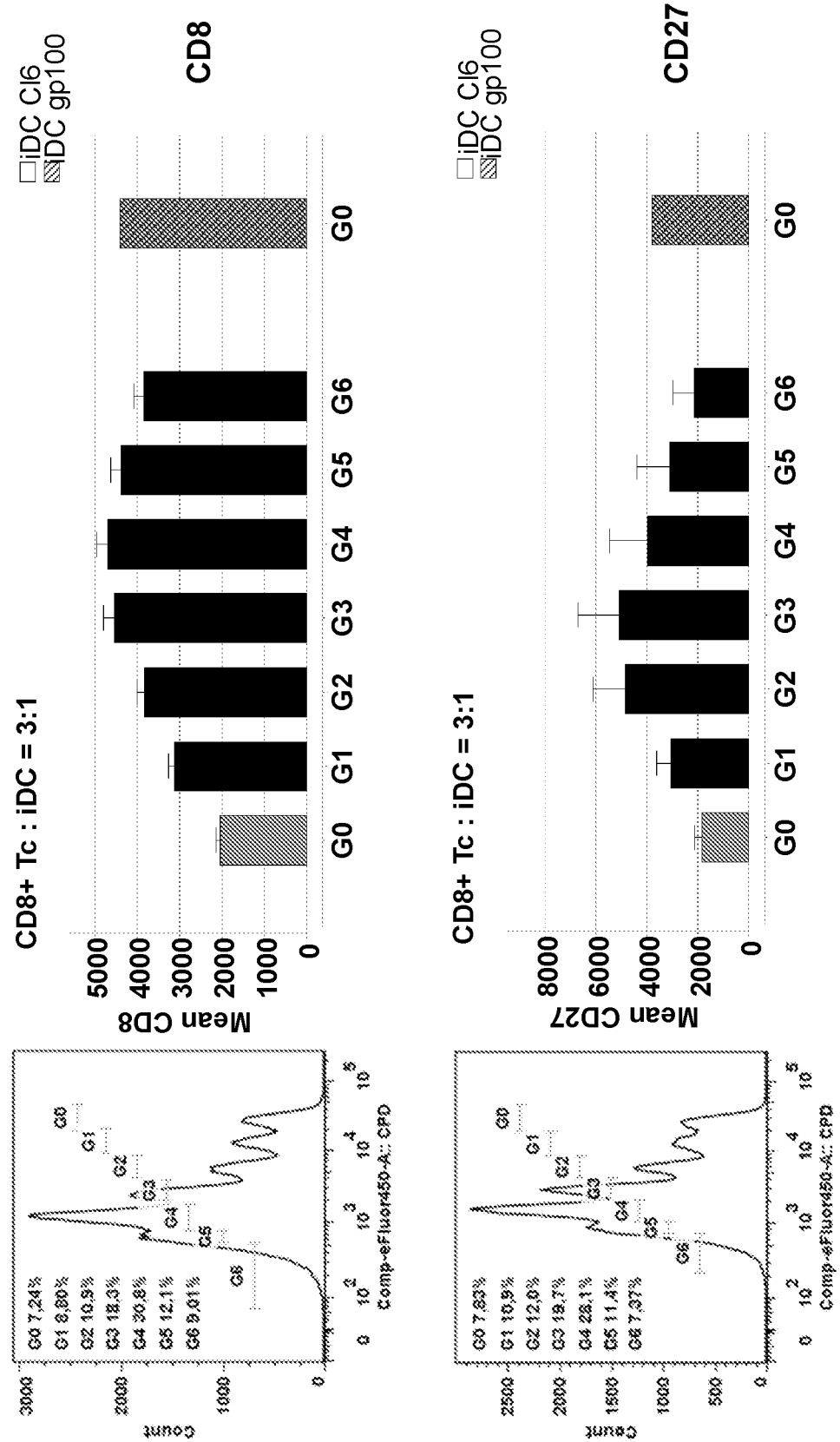
FIG. 6 elicits the upregulation of the costimulatory biomarker CD27 on combinatory TCR-CAR C16-electroporated daughter T-cells after setup of an APC/T-cell coculture. CAR-electroporated T-cells were cocultured for 6 days with C16-electroporated iDCs at an E:T-ratio of 3:1. T-cells were priorly stained with CPD-450 to quantify the dilution of this fluorophor by cell divisions and so, the number and frequency of resulting daughter populations indicated on the left of the histograms in flow cytometry. T-cells were stained with a CD8-specific antibody to exemplify the moderate and equal upregulation of this coreceptor marker for combinatory and classical CARs. In parallel, they were stained with an antibody specific for the costimulatory molecule CD27 to estimate its regulation in parental/daughter populations G0-G6 for all CARs. Although both markers were upregulated roughly 2-fold and additionally, mean expression of CD8 was the same for all CARs, the mean expression of CD27 was much higher for the combinatory CARs, and in particular the inter-combinatory TCR-CAR C16, than the classical CAR. CD27, a biomarker of long-term persistence of T-cells in vivo, reached a much higher plateau for the dim-proliferating T-cells (G2-G4) before expression levels dropped down to basal levels in G6.
Figure 6:
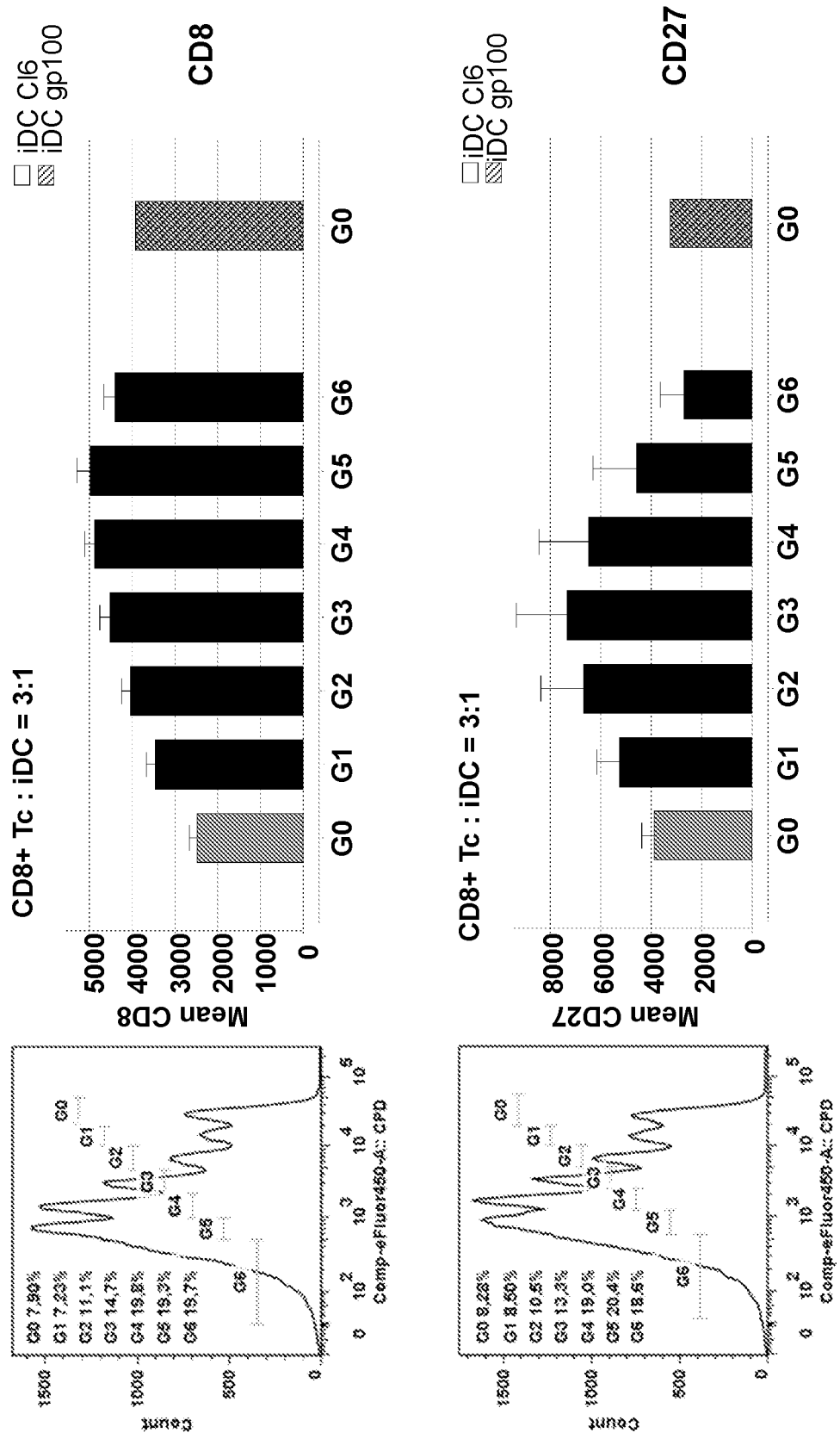
Figure 6:
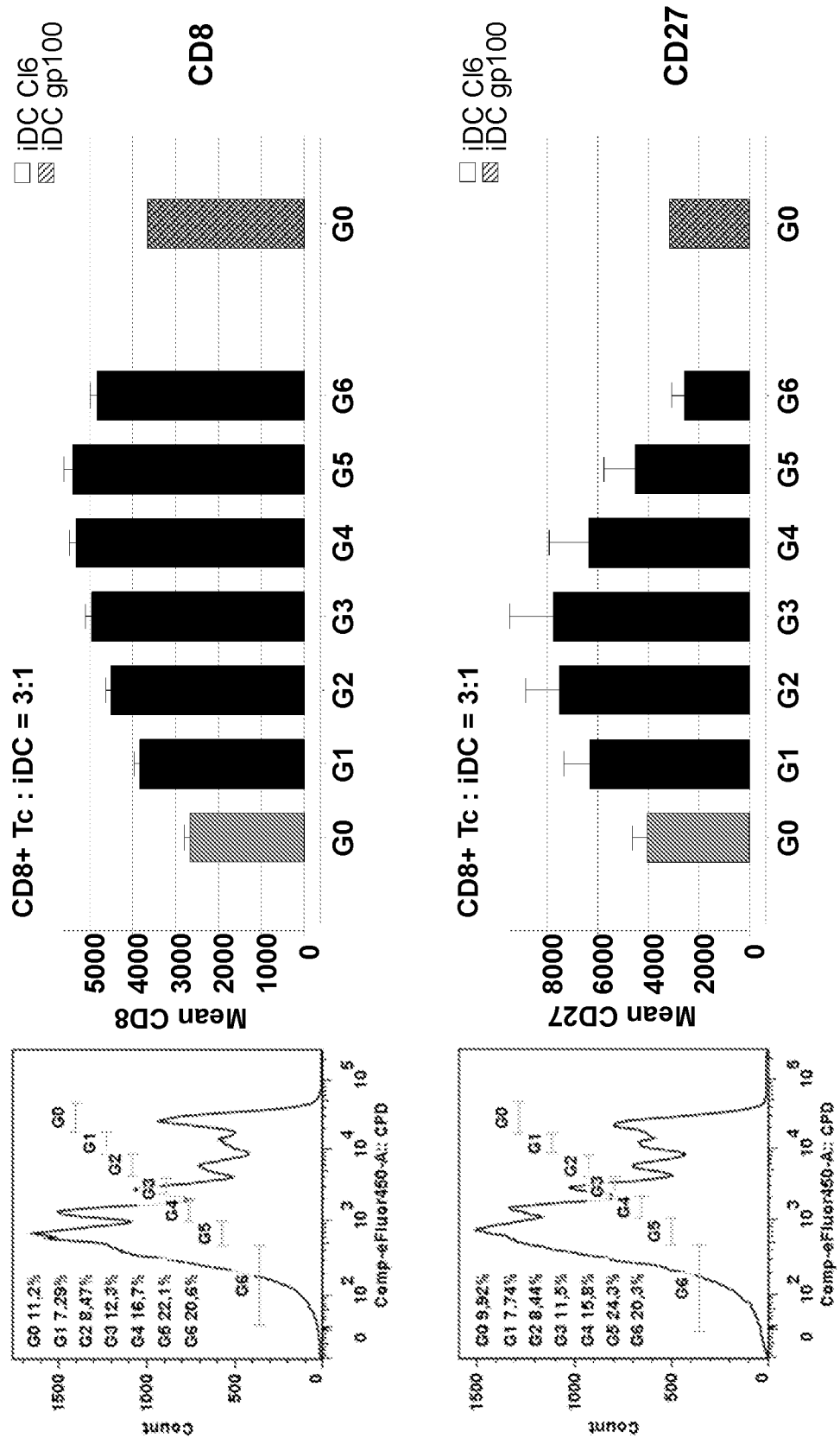

FIG. 6 describes on the left the frequency of proliferating T-cells harnessed with either the classical scCAR (top), the combinatory Cα/β-CAR C16 (center), or the combinatory TCR-CAR C16 silCDR3α (bottom). On the right the mean intensity minus unspecific binding (i.e. isotype binding) for the coreceptor CD8 and the costimulatory receptor CD27 among all parental and daughter populations are shown. T-cells were stained with a CD8-specific antibody to visualize the moderate and almost equal upregulation of this coreceptor marker for combinatory and classical CARs. Hence, CD8-staining may operate as a normalization marker to emphasize the equal regulation of this 'inert' molecule among all CARs scrutinized here. In parallel, they were stained with an antibody specific for the costimulatory molecule CD27 in a different fluorescence-channel to estimate its regulation in parental/daughter populations G0-G6 for all CARs. Although both markers were upregulated roughly 2-fold and additionally, mean expression of CD8 was almost the same for all CARs, the mean expression of CD27 was much higher for the combinatory CARs, and in particular the inter-combinatory TCR-CAR C16, than the classical CAR. CD27, a biomarker of long-term persistence of T-cells in vivo, acquired a much higher plateau for the dim-proliferating T-cells (G2-G4) before expression levels dropped down to basal levels in G6. From this one may hypothesize that combinatory CAR-engineered T-cells may have less of a terminally differentiated and exhausted phenotype (i.e. downregulation of costimulatory molecules) in dim-proliferating populations and hence, may persist longer in vivo. Size (forward scatter) and granulation (side scatter) of cocultured combinatory CAR-electroporated T-cells was even lower than for the classical CAR (data not shown). Hence, a higher upregulation of CD27 is not caused by an increase of the cell surface and hence, by more CD27 on a larger surface.

---

---

We claim:

1. An antigen receptor, which receptor comprises a first peptide chain and a second peptide chain, wherein:

(i) the first peptide chain comprises an immunoglobulin heavy chain variable domain (VH), an immunoglobulin light chain variable domain (VL), a variable region of a T cell receptor chain, and an immunoreceptor signal transmission domain, and the second peptide chain comprises an immunoglobulin heavy chain variable domain (VH), an immunoglobulin light chain variable domain (VL), a variable region of a T cell receptor chain, and an immunoreceptor signal transmission domain, and wherein the VH domain from the first peptide chain forms together with the VL domain from the second peptide chain a first antigen binding site, and wherein the VL domain from the first peptide chain forms together with the VH domain from the second peptide chain a second antigen binding site; or (ii) the first peptide chain comprises two immunoglobulin light chain variable domains (VL), a variable region of a T cell receptor chain, and an immunoreceptor signal transmission domain, and the second peptide chain comprises two immunoglobulin heavy chain variable domains (VH), a variable region of a T cell receptor chain, and an immunoreceptor signal transmission domain, and wherein a first VL domain from the first peptide chain forms a first antigen binding site together with a first VH domain from the second peptide chain, and wherein a second VL domain from the first peptide chain forms a second antigen binding site together with a second VH domain from the second peptide chain.

2. The receptor of claim 1, wherein the immunoreceptor signal transmission domain comprises a constant or invariant region of a T cell receptor chain or a constant or invariant region of an immune cell Fc receptor chain.

3. The receptor of claim 1, wherein the first and/or second peptide chains further comprise a linker between a VL and a VH domain, between two VL domains, between two VH domains, and/or between a VL or VH domain and the variable region of a T cell receptor chain.

4. The receptor of claim 1, wherein (i) the first peptide chain comprises a variable region of a T cell receptor alpha chain and a constant region of a T cell receptor alpha chain and the second peptide chain comprises a variable region of a T cell receptor beta chain and a constant region of a T cell receptor beta chain, or (ii) the first peptide chain comprises a variable region of a T cell receptor beta chain and a constant region of a T cell receptor beta chain and the second peptide chain comprises a variable region of a T cell receptor alpha chain and a constant region of a T cell receptor alpha chain.

5. The receptor of claim 1, wherein the immunoreceptor signal transmission domain is of human origin.

6. The receptor of claim 1, wherein the first and second antigen binding sites bind to different epitopes on the same antigen.

7. The receptor of claim 1, wherein the antigen is a disease-specific antigen.

8. The receptor of claim 7, wherein the antigen is expressed on the surface of a cell.

9. A recombinant cell expressing both, the first and second peptide chains defined in claim 1.

10. A method for producing a cell expressing an antigen receptor which receptor comprises a first peptide chain and a second peptide chain, the method comprising:

(A)
(a) providing a cell;
(b) providing a first genetic construct, wherein the first genetic construct encodes the first peptide chain comprising
an immunoglobulin heavy chain variable domain (VH), an immunoglobulin light chain variable domain (VL), a variable region of a T cell receptor chain, and an immunoreceptor signal transmission domain;

(c) providing a second genetic construct, wherein the second genetic construct encodes the second peptide chain comprising an immunoglobulin heavy chain variable domain (VH), an immunoglobulin light chain variable domain (VL), a variable region of a T cell receptor chain, and an immunoreceptor signal transmission domain;

(d) introducing the first and second genetic constructs into the cell; and (e) allowing the constructs to be expressed in the cell, wherein the VH domain from the first peptide chain is able to form together with the VL domain from the second peptide chain a first antigen binding site, and wherein the VL domain from the first peptide chain is able to form together with the VH domain from the second peptide chain a second antigen binding site; or (B)
(a) providing a cell;
(b) providing a first genetic construct, wherein the first genetic construct encodes the first peptide chain comprising
two immunoglobulin light chain variable domains (VL), a variable region of a T cell receptor chain, and an immunoreceptor signal transmission domain;

(c) providing a second genetic construct, wherein
the second genetic construct encodes the second peptide chain comprising two immunoglobulin heavy chain variable domains (VH), a variable region of a T cell receptor chain, and an immunoreceptor signal transmission domain;

(d) introducing the first and second genetic constructs into the cell; and (e) allowing the constructs to be expressed in the cell; wherein a first VL domain from the first peptide chain is able to form a first antigen binding site together with a first VH domain from the second peptide chain, and wherein a second VL domain from the first peptide chain is able to form a second antigen binding site together with a second VH domain from the second peptide chain.

11. A recombinant cell produced by the method of claim 10.

12. A combination of nucleic acids wherein the first nucleic acid encodes a first peptide chain and a second nucleic acid encodes a second peptide chain, or a nucleic acid encoding both a first and a second peptide chain, wherein (i) the first peptide chain comprises an immunoglobulin heavy chain variable domain (VH), an immunoglobulin light chain variable domain (VL), a variable region of a T cell receptor chain, and an immunoreceptor signal transmission domain, and the second peptide chain comprises an immunoglobulin heavy chain variable domain (VH), an immunoglobulin light chain variable domain (VL), a variable region of a T cell receptor chain, and an immunoreceptor signal transmission domain, and wherein the VH domain from the first peptide chain forms together with the VL domain from the second peptide chain a first antigen binding site, and wherein the VL domain from the first peptide chain forms together with the VH domain from the second peptide chain a second antigen binding site; or (ii) the first peptide chain comprises two immunoglobulin light chain variable domains (VL), a variable region of a T cell receptor chain, and an immunoreceptor signal transmission domain, and the second peptide chain comprises two immunoglobulin heavy chain variable domains (VH), a variable region of a T cell receptor chain, and an immunoreceptor signal transmission domain; and wherein a first VL domain from the first peptide chain forms a first antigen binding site together with a first VH domain from the second peptide chain, and wherein a second VL domain from the first peptide chain is able to form a second antigen binding site together with a second VH domain from the second peptide chain.

13. The combination of nucleic acids or the nucleic acid of claim 12, wherein the nucleic acid is DNA or RNA.

14. A pharmaceutical composition comprising the recombinant cell of claim 9; and a pharmaceutically acceptable carrier.

15. A method for the treatment of a disease comprising administering to a subject a therapeutically effective amount of the pharmaceutical composition of claim 14, wherein the disease is characterized by expression of at least one antigen which is bound by the antigen receptor.

\* \* \* \* \*

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

Gly Gly Gly Gly Ser Gly Gly Gly Gly Ser Gly Gly Gly Gly Ser
1               5                   10                  15